(12) United States Patent
Cozean et al.

(10) Patent No.: US 10,524,997 B2
(45) Date of Patent: Jan. 7, 2020

(54) TOPICAL SANITIZING FORMULATIONS AND USES THEREOF

(71) Applicant: Innovative BioDefense, Inc., Lake Forest, CA (US)

(72) Inventors: Jesse Cozean, Lake Forest, CA (US); Colette Cozean, Lake Forest, CA (US); Susan Goldsberry, Huntington Beach, CA (US)

(73) Assignee: Innovative BioDefense, Inc.

( * ) Notice: Subject to any disclaimer, the term of this patent is extended or adjusted under 35 U.S.C. 154(b) by 0 days.

(21) Appl. No.: 16/010,781

(22) Filed: Jun. 18, 2018

(65) Prior Publication Data

US 2019/0060201 A1 Feb. 28, 2019

Related U.S. Application Data

(63) Continuation of application No. 15/664,542, filed on Jul. 31, 2017, now Pat. No. 10,010,496, which is a continuation of application No. 14/416,010, filed as application No. PCT/US2013/051398 on Jul. 19, 2013, now Pat. No. 9,717,669.

(60) Provisional application No. 61/674,779, filed on Jul. 23, 2012.

(51) Int. Cl.
| | |
|---|---|
| *A61K 31/045* | (2006.01) |
| *A61K 31/14* | (2006.01) |
| *A61K 31/155* | (2006.01) |
| *A61K 31/355* | (2006.01) |
| *A61K 31/717* | (2006.01) |
| *A61K 31/785* | (2006.01) |
| *A61K 8/31* | (2006.01) |
| *A61K 8/34* | (2006.01) |
| *A61K 8/41* | (2006.01) |
| *A61K 8/43* | (2006.01) |
| *A61K 8/67* | (2006.01) |
| *A61K 8/49* | (2006.01) |
| *A61K 45/06* | (2006.01) |
| *A61K 33/30* | (2006.01) |
| *A61K 36/61* | (2006.01) |
| *A61Q 17/00* | (2006.01) |
| *A61Q 19/00* | (2006.01) |
| *A61Q 19/10* | (2006.01) |

(52) U.S. Cl.
CPC .............. *A61K 8/498* (2013.01); *A61K 8/31* (2013.01); *A61K 8/34* (2013.01); *A61K 8/416* (2013.01); *A61K 8/43* (2013.01); *A61K 8/678* (2013.01); *A61K 31/045* (2013.01); *A61K 31/14* (2013.01); *A61K 31/155* (2013.01); *A61K 31/355* (2013.01); *A61K 31/717* (2013.01); *A61K 31/785* (2013.01); *A61K 33/30* (2013.01); *A61K 36/61* (2013.01); *A61K 45/06* (2013.01); *A61Q 17/005* (2013.01); *A61Q 19/007* (2013.01); *A61Q 19/10* (2013.01); *A61K 2800/30* (2013.01)

(58) Field of Classification Search
CPC .... A61K 31/045; A61K 31/14; A61K 31/155; A61K 31/355; A61K 31/717; A61K 31/785; A61K 8/31; A61K 8/34; A61K 8/41; A61K 8/43; A61K 8/67
See application file for complete search history.

(56) References Cited

U.S. PATENT DOCUMENTS

| | | | | |
|---|---|---|---|---|
| 5,708,023 | A * | 1/1998 | Modak | A01N 25/32 514/494 |
| 5,965,610 | A * | 10/1999 | Modak | A01N 25/32 514/494 |
| 8,207,148 | B2 * | 6/2012 | Modak | A61K 8/27 424/641 |
| 2005/0019431 | A1 * | 1/2005 | Modak | A01N 33/12 424/736 |
| 2005/0095261 | A1 * | 5/2005 | Popp | A61K 8/4926 424/400 |
| 2006/0204466 | A1 * | 9/2006 | Littau | A01N 31/02 424/70.13 |
| 2010/0278906 | A1 * | 11/2010 | Sondgeroth | A61K 8/416 424/450 |
| 2011/0028563 | A1 * | 2/2011 | Found | A01N 33/12 514/642 |
| 2011/0257125 | A1 * | 10/2011 | Schaefer | A61K 9/0048 514/54 |
| 2012/0260820 | A1 * | 10/2012 | Modak | A61K 8/27 106/18.32 |

* cited by examiner

*Primary Examiner* — Zohreh A Fay
(74) *Attorney, Agent, or Firm* — Sheppard Mullin Richter & Hampton LLP

(57) ABSTRACT

Several embodiments disclosed herein relate to formulations having antimicrobial and/or sanitizing effects, and uses of the same. In particular, the formulations and methods of using same provide, in several embodiments, an immediate and a persistent antimicrobial effect against a broad spectrum of microorganisms.

18 Claims, 9 Drawing Sheets

TOPICAL SANITIZING FORMULATIONS AND USES THEREOF

CROSS REFERENCE TO RELATED APPLICATIONS

This application is a continuation of U.S. patent application Ser. No. 15/664,542, filed Jul. 31, 2017, now issued as U.S. Pat. No. 10,010,496 on Jul. 3, 2018, which is a continuation of U.S. patent application Ser. No. 14/416,010, filed Jan. 20, 2015, now issued as U.S. Pat. No. 9,717,669 on Aug. 1, 2017, which is the U.S. National Stage under 35 U.S.C. § 371 of International Application No. PCT/US2013/051398, filed Jul. 19, 2013, which claims the benefit of U.S. Provisional Application No. 61/674,779, filed on Jul. 23, 2012, the entire disclosure of each of which is incorporated by reference herein.

BACKGROUND

Field

Several embodiments of the inventions disclosed herein relate to formulations having antimicrobial effects, and uses of the same. In some embodiments, the formulations are used to kill, inhibit, and/or otherwise reduce the number, activity and/or growth of microorganisms.

Description of the Related Art

Microorganisms (or microbes) are single cell, cell cluster, or multicellular microscopic (or macroscopic) organisms including but not limited to, bacteria, fungi, archaea, protists, plants (e.g., green algae), viruses, prions, parasites, and animals (e.g. amoeba, plankton). Microorganisms may be beneficially exploited in a variety of fields, such as biotechnology, food and beverage preparation, and diagnostic technologies. In other contexts, however, short or long-term exposure to microorganisms may be harmful and lead to one or more of a variety of illnesses and diseases in plants, animals, and humans.

SUMMARY

Contamination of surfaces with one or more types of microorganisms, and/or the transfer of microorganisms between surfaces can lead to a variety of negative effects, including but not limited to illness, disease, passage of disease, increased medical care costs, and/or loss of work time and associated loss of revenue. To address such issues and reduce the presence of a broad spectrum of microorganisms from a variety of surfaces, there is provided herein a method of dual-action immediate and persistent microbial reduction, the method comprising, applying a topical formulation to a surface contaminated with both gram-positive and gram-negative bacteria. In one embodiment, the topical formulation comprises, consists essentially of, or consists of a terpene, tocopheryl acetate, polyaminopropyl biguanide and at least one quaternary ammonium salt selected from the group consisting of benzethonium chloride and benzalkonium chloride, wherein the formulation kills (or otherwise inactivates) at least 90% (e.g., 99%) of both gram-positive and gram-negative bacteria within 45 seconds (e.g., 20 seconds) of contact with the microbes. The formulation is configured to kill (or otherwise inactivate) at least 85% (e.g., 90%) of both gram-positive and gram-negative bacteria at least 4 hours post-application of the formulation in one embodiment. In one embodiment, the effect persists for at least 6 or 8 hours post-application. Persistence, according to some embodiments, is achieved by a non-evaporative component of the formulation. Advantageously, in several embodiments, an antimicrobial component remains on the surface (hands, equipment, etc.) that deters against any subsequent contamination. This persistent antimicrobial barrier may be physical, chemical or both, and persists, in some embodiments, even after the surface is rinsed. Thus, in one embodiment, the persistent barrier is water-proof or water-resistant.

Triclosan-free formulations are provided in several embodiments. Many embodiments disclosed herein are particularly advantageous because they are efficacious without contributing to microbial drug resistance.

In several embodiments, a method of dual-action immediate and persistent microbial reduction is provided. In one embodiment, the method comprises applying a topical formulation to a surface contaminated with a plurality of microbes. In one embodiment, the topical formulation comprises, consists essentially of or consists of a terpene, tocopheryl acetate, polyaminopropyl biguanide and at least one quaternary ammonium salt selected from the group consisting of benzethonium chloride and benzalkonium chloride, wherein the formulation kills (or otherwise inactivates) at least 90% (e.g., 99%) of the plurality of microbes within 45 seconds (e.g., 20 seconds) of contact with the microbes. In one embodiment, the formulation is configured to kill (or otherwise inactivate) at least 85% (e.g., 90%) of the plurality of microbes at least 4 hours post-application of the formulation, wherein the plurality of microbes comprises two or more of the following: gram-positive bacteria, gram-negative bacteria, fungi, mold, yeast and viruses. In one embodiment, the effect persists for at least 6 or 8 hours post-application.

The methods disclosed herein are useful for providing antimicrobial effects to a variety of surfaces. In several embodiments, the surface is human or animal skin or an inorganic surface (including but not limited to countertops, door handles, faucets, telephones beds/bed frames, bed linens, medical equipment, computers, writing instruments, surgical equipment). In several embodiments, the surface is human or animal skin, and wherein the application does not induce skin irritation. Advantageously, in several embodiments, the formulations not only provide antimicrobial effects, but also moisturize, soften, and/or improve the health of the human and/or animal skin to which they are applied. In several embodiments, the formulations are also used to facilitate wound healing (e.g., by reducing or preventing infection). In several embodiments, the formulations are used to treat acne, which in several embodiments, is particularly advantageous because the certain embodiments of the formulations disclosed herein moisturize the skin (e.g., are without drying effects). In several embodiments, fungal infections can be treated and/or prevented by application of the formulations disclosed herein.

In several embodiments, the topical formulation dries within about 5 to about 30 seconds. In some embodiments, shorter or longer drying times are provided (e.g., about 5 to about 10 seconds, about 10 to about 15 seconds, about 15 to about 20 seconds, about 20 to about 25 seconds, about 25 to about 30 seconds, and overlapping ranges thereof). In some embodiments, the drying time assists in the "feel" of the formulation on the skin, in that, for example, there is a reduction in the residue or sticky, greasy, or otherwise unclean feeling that other formulations may leave on a surface.

In several embodiments, the bacteria comprise transient bacteria, while in other embodiments the formulations can be adjusted to provide antimicrobial effects against certain resident bacteria.

In several embodiments, the terpene is present in the topical formulation in an amount ranging from about 0.25% to about 0.60% by weight of the formulation. In some embodiments, the tocopheryl acetate is present in the topical formulation in an amount ranging from about 0.05% to about 0.5% by weight of the formulation. In some embodiments, the polyaminopropyl biguanide is present in an amount ranging from about 0.05% to about 0.20% by weight of the formulation. In some embodiments, the at least one quaternary ammonium salt is present in an amount ranging from about 0.01% to about 0.40% by weight of the formulation. In several embodiments, the quaternary ammonium salt comprises benzethonium chloride. Benzalkonium chloride, or another quaternary ammonium salt, may be used instead of or in addition to benzethonium chloride in some embodiments.

In several embodiments, the formulation further comprises alcohol in an amount ranging from about 8% to about 20% by weight of the formulation. In several embodiments the formulation may also further comprise chlorhexidine gluconate in an amount ranging from about 0.10% to about 0.40% by weight of the formulation. The formulation, depending on the embodiment may also further comprise hydroxyethyl ethylcellulose in an amount ranging from about 0.05% to about 0.20% by weight of the formulation. In some embodiments, the formulation further comprises one or more zinc salts in an amount ranging from about 0.05% to about 0.60% by weight of the formulation. In some embodiments, the zinc salt comprises zinc lactate, zinc gluconate, combinations thereof, and/or a zinc matrix. In several embodiments, the formulation further comprises panthenol in an amount ranging from about 0.25% to about 0.60% by weight of the formulation. In several embodiments, the terpene comprises a sesquiterpene, and in certain such embodiments, the sesquiterpene comprises farnesol. Other terpenes, or combinations of terpenes (and/or their derivatives) are used in some embodiments.

In several embodiments, the formulation further comprises one or more additional compounds, such as emollients. In some embodiments, the formulation further comprises one or more of Vitamins A, B, K, C, and aloe. In several embodiments, the topical formulation further comprises an essential oil, such as for example, eucalyptus oil. In some embodiments, the eucalyptus oil is present in an amount ranging from about 0.05% to about 0.5% by weight of the formulation. Other essential oils, alone or in combination, may also be used.

In several embodiments, application of the topical formulation comprises dispensing between about 0.1 and about 0.8 mL (e.g., about 0.1 mL and about 0.2 mL, about 0.2 mL and about 0.3 mL, about 0.3 mL and about 0.4 mL, about 0.4 mL and about 0.5 mL, about 0.5 mL and about 0.6 mL, about 0.6 mL and about 0.7 mL, about 0.7 mL and about 0.8 mL, and overlapping ranges thereof) of the formulation onto the surface. Advantageously, in several embodiments, the efficacy of the formulation at 4 hours (or more) post-application of the formulation is achieved in the absence of reapplication of the formulation to the surface.

There is further provided, in several embodiments, a method of dual-action immediate and persistent microbial reduction, the method comprising applying a topical formulation to a surface contaminated with a plurality of microbes, the topical formulation comprising a terpene, polyaminopropyl biguanide and at least one quaternary ammonium salt selected from the group consisting of benzethonium chloride and benzalkonium chloride (or a combination thereof), wherein the formulation kills at least 99% of the plurality of microbes within 20 seconds (e.g., within 2, 5, 10, 15 seconds) of contact with the microbes, wherein the formulation is configured to kill at least 90% of the plurality of microbes at least 4 hours (or more) post-application of the formulation, and wherein the plurality of microbes comprises two or more of the following: gram-positive bacteria, gram-negative bacteria, fungi, and viruses.

Moreover, there is provided a method of dual-action immediate and persistent microbial reduction, the method comprising, applying a topical formulation to a surface contaminated with both gram-positive and gram-negative bacteria, wherein the topical formulation comprises a terpene, polyaminopropyl biguanide and at least one quaternary ammonium salt selected from the group consisting of benzethonium chloride and benzalkonium chloride, wherein the formulation kills at least 99% of the plurality of microbes within 20 seconds (e.g., within 2, 5, 10, 15 seconds) of contact with the microbes, wherein the formulation is configured to kill at least 95% of the plurality of microbes at least 4 hours (or more) post-application of the formulation, and wherein the formulation is configured to kill at least 90% of both gram-positive and gram-negative bacteria at least 4 hours (or more) post-application of the formulation. There is additionally provided a method of dual-action immediate and persistent microbial reduction, the method comprising, applying a topical formulation to a surface contaminated with a plurality of microbes, wherein the topical formulation comprises a terpene, polyaminopropyl biguanide and at least one quaternary ammonium salt selected from the group consisting of benzethonium chloride and benzalkonium chloride, wherein the formulation kills at least 99% of the plurality of microbes within 20 seconds of contact with the microbes, wherein the formulation is configured to kill at least 90% of the plurality of microbes at least 4 hours post-application of the formulation, and wherein the plurality of microbes comprises two or more of the following: gram-positive bacteria, gram-negative bacteria, fungi, and viruses.

In several embodiments, the topical formulation further comprises alcohol in an amount ranging from about 60% to about 90% by weight of the formulation. In several embodiments, the formulation is suitable for application to a surface that is human or animal skin or an inorganic surface. In those cases where the is human or animal skin, and wherein the application does not induce skin irritation, which includes but is not limited to drying, cracking, reddening, itchiness, burning or other adverse sensations.

In several embodiments, the terpene is present in the topical formulation in an amount ranging from about 0.25% to about 0.60% by weight of the formulation. In some embodiments, the tocopheryl acetate is present in the topical formulation in an amount ranging from about 0.05% to about 0.5% by weight of the formulation. In some embodiments, the polyaminopropyl biguanide is present in an amount ranging from about 0.05% to about 0.20% by weight of the formulation. In some embodiments, at least one quaternary ammonium salt is present in an amount ranging from about 0.01% to about 0.40% by weight of the formulation. In several embodiments, the quaternary ammonium salt comprises benzethonium chloride. Benzalkonium chloride and/or another quaternary ammonium salt may be used in additional embodiments.

In several embodiments, the formulation further comprises alcohol in an amount ranging from about 8% to about 20% by weight of the formulation. In several embodiments the formulation may also further comprise chlorhexidine gluconate in an amount ranging from about 0.10% to about 0.40% by weight of the formulation. The formulation, depending on the embodiment may also further comprise hydroxyethyl ethylcellulose in an amount ranging from about 0.05% to about 0.20% by weight of the formulation. In some embodiments, the formulation further comprises one or more zinc salts in an amount ranging from about 0.05% to about 0.60% by weight of the formulation. In some embodiments, the zinc salt comprises zinc lactate, zinc gluconate, combinations thereof, and/or a zinc matrix. In several embodiments, the formulation further comprises panthenol in an amount ranging from about 0.25% to about 0.60% by weight of the formulation. In several embodiments, the terpene comprises a sesquiterpene, and in certain such embodiments, the sesquiterpene comprises farnesol. Other terpenes, or combinations of terpenes (and/or their derivatives) are used in some embodiments.

In several embodiments, the formulation further comprises one or more additional emollient compounds. In some embodiments, the formulation further comprises one or more of Vitamins A, B, K, E, and C. In several embodiments, the topical formulation further comprises an essential oil, such as for example, eucalyptus oil. In some embodiments, the eucalyptus oil is present in an amount ranging from about 0.05% to about 0.5% by weight of the formulation. Other essential oils, alone or in combination, may also be used.

In several embodiments, application of the topical formulation comprises dispensing between about 0.1 mL and about 0.8 mL (e.g., about 0.1 mL and about 0.2 mL, about 0.2 mL and about 0.3 mL, about 0.3 mL and about 0.4 mL, about 0.4 mL and about 0.5 mL, about 0.5 mL and about 0.6 mL, about 0.6 mL and about 0.7 mL, about 0.7 mL and about 0.8 mL, and overlapping ranges thereof) of the formulation onto the surface. Advantageously, in several embodiments, the efficacy of the formulation at 2-8 hours (e.g., 6 hours) post-application of the formulation is achieved in the absence of reapplication of the formulation to the surface. In several embodiments, efficacy of the formulation persists for longer periods of time, even in the absence of reapplication.

There is additionally provided a method of immediate microbial reduction, the method comprising applying a topical formulation to a surface contaminated with both gram-positive and gram-negative bacteria, wherein the topical formulation comprises a terpene, tocopheryl acetate, polyaminopropyl biguanide and at least one quaternary ammonium salt selected from the group consisting of benzethonium chloride and benzalkonium chloride, wherein the formulation kills at least 90% of both gram-positive and gram-negative bacteria within 20 seconds (e.g., within 2, 5, 10, 15 seconds) of contact with the microbes. Further, there is provided a method of immediate microbial reduction, the method comprising, applying a topical formulation to a surface contaminated with a plurality of microbes, wherein the topical formulation comprises a terpene, tocopheryl acetate, polyaminopropyl biguanide and at least one quaternary ammonium salt selected from the group consisting of benzethonium chloride and benzalkonium chloride, wherein the formulation kills at least 90% of the plurality of microbes within 20 seconds (e.g., within 2, 5, 10, 15 seconds) of contact with the microbes, and wherein the plurality of microbes comprises two or more of the following: gram-positive bacteria, gram-negative bacteria, fungi, and viruses.

In still additional embodiments, there are provided method for the immediate and persistent reduction in microbial populations, the methods comprising applying an alcohol-based topical formulation to a surface contaminated with both gram-positive and gram-negative bacteria, wherein the topical formulation comprises at least about 65% ethyl alcohol by weight, polyaminopropyl biguanide and at least one quaternary ammonium salt selected from the group consisting of benzethonium chloride and benzalkonium chloride. In several embodiments, the application of the formulation results in a reduction of least 95% (e.g., 99%) of both gram-positive and gram-negative bacteria within 45 seconds (e.g., 20 seconds) of contact with the bacteria, and wherein application of the formulation also result in a reduction of at least 80% (e.g., 90%, 95%) of both gram-positive and gram-negative bacteria at least 2 hours (e.g., 3 hours, 4 hours) post-application of the formulation. In several embodiments, the significant efficacy persists between the immediate and persistent time frames, e.g., there is significant antimicrobial efficacy at about 10 minutes, about 20 minutes, about 25 minutes, about 30 minutes, about 35 minutes, about 40 minutes, about 60 minutes, or about 90 minutes (and times therebetween) after application.

In several embodiments, there are also provided methods for preventing bacterial colonization of a surface (such as human skin), the method comprising applying a topical formulation to a surface susceptible to contamination with both bacteria, wherein the topical formulation comprises a terpene, tocopheryl acetate, polyaminopropyl biguanide, chlorhexidine digluconate, and at least one quaternary ammonium salt selected from the group consisting of benzethonium chloride and benzalkonium chloride. In several embodiments, the formulation kills at least 99% of the bacteria within 20 seconds of contact with the microbes (resulting in short-term prevention of colonization) and kills at least 85% of both gram-positive and gram-negative bacteria at least 8 hours post-application of the formulation (resulting in prevention of colonization on a long-term time frame). In some embodiments, the formulation kills at least 95% of the bacteria within about 45 seconds of contact with the microbes (resulting in short-term prevention of colonization) and kills at least 80% of both gram-positive and gram-negative bacteria at least 6, 8, 12, or 24 hours post-application of the formulation (resulting in prevention of colonization on a long-term time frame). In other words, gram-positive and gram-negative bacteria continue to be inhibited even after 6 hours post application of the formulation. In some embodiments, this time period is lengthened to, for example, 8 hours, 12 hours or 24 hours.

In several embodiments, the persistence of the formulations is due to, at least in part, the continued presence of the formulations on a surface (such as the hands of a user). In several embodiments, the continued presence of the formulation is due to chemical or physical interactions between the components of the formulation and the surface. For example, in several embodiments wherein the formulations are applied to the skin of a user, the formulation ionically binds to the skin of the user. Thus, the formulation is present on the skin of the user for a longer period of time than, for example many alcohol based products whose efficacy is significantly, if not completely, diminished upon evaporation of the alcohol. In several embodiments, reversible covalent bonding occurs between the formulation and the skin of the user. Advantageously, in several embodiments, the continued presence of the formulations is not associated with adverse feel or residue (e.g., no sticky or greasy hand feel). Moreover, in several embodiments, the formulations are configured to remain on the surface after exposure of the surface to conditions that would result in the substantial removal of other products. For example, in several embodiments, even after multiple (e.g., 3, 4, 5, 6, or more) hand washings, a significant percentage of the formulations remain on the hands of a user (e.g., at least about 80%, about at least 70%, at least about 60 percent, at least about 50%, and percentages therebetween). Advantageously, in several embodiments, even if the handwashing does result in reduction in the presence of the formulations on a surface (e.g., the hands of the user), the efficacy of the formulation persists. For example, in several embodiments, reduction in the amount of the formulation that remains on a subject's hands can be reduced by about 20%, about 40%, about 60%, about 80% (or greater) while substantial efficacy of the formulation is maintained. Thus, in several embodiments, the persistence allows the formulations to remain present on the surface that has been treated, such that the surface is resistant to microbial colonization for an extended period of time, even without reapplication of the formulations. In several embodiments, the formulations can be reapplied, which results in further protection of the surface.

In several embodiments, there are additionally provided methods of treating a surface colonized with microbes by applying a topical formulation to a colonized surface, wherein the topical formulation comprises a terpene, polyaminopropyl biguanide, a zinc salt, and at least one quaternary ammonium salt selected from the group consisting of benzethonium chloride and benzalkonium chloride. Treatment of the surface with the formulation, in several embodiments, results in at least a 95% (e.g., 99%) reduction of the microbe population within 45 seconds (e.g., 20 seconds) of contact with the microbes, and surprisingly, continues to result in at least 90% reduction in the microbe population at time points of at least 4 hours post-application of the formulation. In some embodiments, the reduction of 90% reduction is also seen at 8 hours, 12 hours or 24 hours.

In several embodiments of the formulations described herein, microbial reduction levels drop by 1-5% every hour. As an example, if a 99% reduction in microbes is observed at hour 0 (immediately post application of the formulation), a 98% reduction is seen at hour 1, a 97% reduction is seen at hour 2, a 96% reduction is seen at hour 3, a 95% reduction is seen at hour 4, etc. In one embodiment, this reduction trend lasts for the first 12, 18 or 24 hours. The percent reduction is compared to the number and/or function of microbes pre-application of an antimicrobial formulation described herein.

In view of the continued development of resistance to antibiotics of certain microbe populations, there is also advantageously provided herein methods for the dual-action immediate and persistent reduction of antibiotic resistant bacteria, the method comprising applying a topical formulation to a surface contaminated with antibiotic resistant bacteria, wherein the topical formulation comprises a terpene, polyaminopropyl biguanide, a zinc salt, and at least one quaternary ammonium salt selected from the group consisting of benzethonium chloride and benzalkonium chloride. Application of the formulation results in a short term (e.g., within about 120 seconds) kill of at least 99% of the antibiotic resistant bacteria, and a long-term (e.g., for at least about 6 hours after application of the formulation) kill of at least 80% of the antibiotic resistant bacteria.

Also provided is a method of reduction of antibiotic resistant bacteria on a short and long-term basis comprising applying a topical formulation to a surface contaminated with antibiotic resistant bacteria, wherein the topical formulation comprises at least about 65% ethyl alcohol by weight, polyaminopropyl biguanide and at least one quaternary ammonium salt selected from the group consisting of benzethonium chloride and benzalkonium chloride. Application of the formulation results in a short term (e.g., within about 120 seconds) kill of at least 99% of the antibiotic resistant bacteria, and a long-term (e.g., for at least about 6 hours after application of the formulation) kill of at least 80% of the antibiotic resistant bacteria. Additionally provided are methods of reduction of drug-resistant viruses on a short and long-term basis comprising applying a formulation to a surface contaminated with drug-resistant viruses, wherein the topical formulation comprises ethyl alcohol, polyaminopropyl biguanide and at least one quaternary ammonium salt selected from the group consisting of benzethonium chloride and benzalkonium chloride. In still additional embodiments, the topical formulations disclosed herein are used to eliminate viruses from a surface, without inducing resistance to the formulation in the viruses.

Moreover, several embodiments relate to methods of reducing bacterial contamination of a surface, without intruding bacterial resistance, the method comprising applying a topical formulation to a surface each time that surface is contaminated with the bacteria, wherein the topical formulation comprises a terpene, polyaminopropyl biguanide and at least one quaternary ammonium salt selected from the group consisting of benzethonium chloride and benzalkonium chloride, wherein the formulation kills at least 90% of the bacteria after a first contamination, and wherein the formulation kills at least 99.9% of the bacteria after at least 9 additional contaminations of the surface. Advantageously such formulations and methods can be used to repeatedly decontaminate a surface of microbes, without loss of efficacy against the microbes, despite repeated applications. Additionally, several embodiments relate to methods of reducing viral contamination of a surface, without intruding viral drug resistance, the method comprising applying a topical formulation to a surface each time that surface is contaminated with the virus (or viruses), wherein the formulation comprises a terpene, polyaminopropyl biguanide and at least one quaternary ammonium salt selected from the group consisting of benzethonium chloride and benzalkonium chloride. As above, advantageously such formulations and methods can be used to repeatedly decontaminate a surface of virus (even of distinct viral types), without loss of efficacy against the viruses, despite repeated applications. Such methods are of particular importance in environments where repeated contamination is possible, such as, for example, health care facilities. Additionally, the methods and formulations (discussed in more detail below) can be used in other arenas, such as for example, schools or workplaces (to reduce absenteeism), food preparation areas (to reduce food contamination), as well as other environments where microbial contamination is possible. Moreover, in several embodiments, the efficacy of the formulations is such that smaller amounts may be used to generate efficacy equivalent to that of other products (which require larger application amounts). Thus, several embodiments of the formulations provide effective protection against microbial contamination, but at significant cost savings.

In several embodiments, the formulations described herein are configured in a form selected from the group consisting of a powder, spray, sanitizer, scrub, gel, lotion, cream, foaming soap, and block soap. In additional embodiments, the formulation is suitable for incorporation into an additional formulation selected from the group consisting of body wash, shampoo, conditioner, and cosmetic base.

Although several topical formulations are provided, non-topical formulations are also provided (e.g., oral, systemic, inhalants, etc.). In some embodiments, formulations described herein are embedded within or coated on to materials. Antimicrobial wipes are provided in several embodiments. In some embodiments, wipes comprise a single layer or multiple layers that are woven or non-woven. Materials include but are not limited to natural or synthetic materials such as cotton, soya, hemp, rayon, polyester, nylon or other polymers. The wipes can be wet or dry. Wipes (or sponges) may be provided with or without a handle. Wipes may include several of the formulations described herein. Wipes may be suitable for skin or surfaces (floors, counters, lavatories). For human use, wipes may include emollient or other dermatologically beneficial ingredients.

In addition to the methods and processes disclosed herein, there are also provided antimicrobial formulations that provide unexpectedly advantageous antimicrobial effects, on an immediate time frame, a persistent time frame, and/or an immediate and a persistent time frame. Thus, there is provided, in several embodiments, a dual-action antimicrobial formulation for both immediate and persistent reduction of gram-positive and gram-negative bacteria, the formulation comprising, consisting essentially of or consisting of a quaternary ammonium salt in an amount ranging from about 0.10% to about 0.40% by weight of the formulation, wherein the quaternary ammonium salt comprises benzethonium chloride, benzalkonium chloride, or combinations thereof, a terpene or derivative thereof in an amount ranging from about 0.25% to about 0.60% by weight of the formulation, tocopheryl acetate in an amount ranging from about 0.05% to about 0.5% by weight of the formulation, polyaminopropyl biguanide in an amount ranging from about 0.05% to about 0.20% by weight of the formulation, wherein the formulation kills at least 99% of both gram-positive and gram-negative bacteria within 20 seconds of contact with the microbes, and wherein the formulation is configured to kill at least 90% of both gram-positive and gram-negative bacteria at least 4 hours post-application of the formulation. In several embodiments, the formulations comprise, consist of, or consist essentially of natural ingredients (e.g., non-synthetic). Combinations of natural and synthetic ingredients are used in additional embodiments.

There is also provided a dual-action antimicrobial formulation for both immediate and persistent reduction of broad spectrum microbes, the formulation comprising, consisting essentially of or consisting of a quaternary ammonium salt in an amount ranging from about 0.10% to about 0.40% by weight of the formulation, wherein the quaternary ammonium salt comprises benzethonium chloride, benzalkonium chloride, or combinations thereof, a terpene or derivative thereof in an amount ranging from about 0.25% to about 0.60% by weight of the formulation, tocopheryl acetate in an amount ranging from about 0.05% to about 0.5% by weight of the formulation, polyaminopropyl biguanide in an amount ranging from about 0.05% to about 0.20% by weight of the formulation, wherein the formulation kills at least 99% of a plurality of microbes within 20 seconds of contact with the microbes, wherein the formulation is configured to kill at least 90% of the plurality of microbes at least 4 hours post-application of the formulation, and wherein the plurality of microbes comprises two or more of the following: gram-positive bacteria, gram-negative bacteria, fungi, and viruses.

In several embodiments, a sanitizing gel or non-gel formulation is provided comprising, consisting essentially of, or consisting of (by weight of the formulation) deionized water in an amount ranging from about 20% to about 30% (e.g., 26.98%), D,L panthenol in an amount ranging from about 0.2% to about 2.0% (e.g., 1.0%), Structure CEL (comprising hydroxyethyl ethylcellulose, water, sodium sulfate, sodium citrate, BHT) in an amount ranging from about 0.4% to about 1.0% (e.g., 0.7%), 200 proof denatured alcohol in an amount ranging from about 60% to about 75% (e.g., 69.0%), PEG-12 dimethicone in an amount ranging from about 0.1% to about 0.3% (e.g., 0.2%), farnesol in an amount ranging from about 0.1% to about 1.0% (e.g., 0.5%), benzethonium chloride in an amount ranging from about 0.05% to about 0.2% (e.g., 0.12%), and cosmocil CQ (comprising water and polyaminopropyl biguanide) in an amount ranging from about 0.5% to about 3% (e.g., 1.5%).

In several embodiments, a non-gel sanitizer lotion is provided comprising, consisting essentially of or consisting of (by weight of the formulation) deionized water in an amount ranging from about 60% to about 75% (e.g., 69.36%), polyquaternium-10 in an amount ranging from about 0.05% to about 1.0% (e.g., 0.1%), glycerine in an amount ranging from about 1.5% to about 3.5% (e.g., 2.75%), D,L panthenol in an amount ranging from about 0.1% to about 2% (e.g., 0.5%), zinc gluconate in an amount ranging from about 0.1% to about 2% (e.g., 0.3%), incroquat behenyl TMS in an amount ranging from about 3.0% to about 5.0% (e.g., 4.2%), stearamidopropyl dimethylamine in an amount ranging from about 0.5% to about 2% (e.g., 0.84%), cetearyl alcohol in an amount ranging from about 3.0% to about 5.0% (e.g., 3.8%), dimethicone in an amount ranging from about 0.5% to about 2.0% (e.g., 1.0%), farnesol in an amount ranging from about 0.1% to about 2% (e.g., 0.5%), tocopheryl acetate in an amount ranging from about 0.01 to about 1.0% (e.g., 0.1%); citric acid in an amount ranging from about 0.01% to about 1.0% (e.g., 0.15%), benzethonium chloride in an amount ranging from about 0.1% to about 1.5% (e.g., 0.2%); euxyl K 700 (comprising benzyl alcohol, phenoxyethanol, potassium sorbate, tocopherol) in an amount ranging from about 0.1% to about 1.5% (e.g., 0.5%), 200-proof alcohol in an amount ranging from about 10.0% to about 20.0% (e.g., 14.0%), chlorhexidine digluconate in an amount ranging from about 0.1% to about 1.0% (e.g., 0.2%), and cosmocil CQ (comprising water and polyaminopropyl biguanide) in an amount ranging from about 0.05% to about 3.0% (e.g., 1.5%).

In several embodiments, a non-gel sanitizer is provided. Many of the formulations described herein are provided in non-gel formats, and are particularly advantageous in being more liquid or more solid than typical gels.

In several embodiments, a surgical scrub is provided comprising (by weight of the formulation) deionized water in an amount ranging from about 20.0% to about 30.0% (e.g., 27.68%), D,L-panthenol in an amount ranging from about 0.5% to about 2.0% (e.g., 1.0%), PEG-12 dimethicone in an amount ranging from about 0.05% to about 0.5% (e.g., 0.2%), farnesol in an amount ranging from about 0.1% to about 2.0% (e.g., 0.5%), 200 proof alcohol in an amount ranging from about 60% to about 75% (e.g., 69.0%), cosmocil CQ (comprising water and polyaminopropyl biguanide) in an amount ranging from about 0.5% to about 3.0% (e.g., 1.5%), and benzethonium chloride in an amount ranging from about 0.05% to about 1.0% (e.g., 0.12%).

In several embodiments, a persistent foaming soap is provided comprising (by weight of the formulation) deionized water in an amount ranging from about 50.0% to about 65.0% (e.g., 64.02%), polyquaternium-10 in an amount ranging from about 0.005% to about 0.1% (e.g., 0.01%), citric acid in an amount ranging from about 0.1% to about 2.0% (e.g., 0.7%), butylene glycol in an amount ranging from about 0.5% to about 2.0% (e.g., 1.0%), zinc gluconate in an amount ranging from about 0.1% to about 2.0% (e.g., 0.3%), benzethonium chloride in an amount ranging from about 0.05% to about 2.0% (e.g., 0.2%), mackamine LO (comprising water and lauramine oxide) in an amount ranging from about 5.0% to about 10.0% (e.g., 8.0%), caltaine C-35 (comprising water cocamiopropyl betaine, and sodium chloride) in an amount ranging from about 5.0% to about 10.0% (e.g., 7.0%), carsoquat CT-429 (comprising water and cetrimonium chloride) in an amount ranging from about 3.0% to about 10.0% (e.g., 5.0%), PPG-2 hydroxyethyl cocamide in an amount ranging from about 1.0% to about 5.0% (e.g., 3.0%), methylchloroisothiazolinone in an amount ranging from about 0.01% to about 1.0% (e.g., 0.07%), actiphyte of aloe vera (comprising glycerin, water aloe barbadensis leaf extract) in an amount ranging from about 0.05% to about 1.0% (e.g., 0.1%), 200 proof alcohol in an amount ranging from about 5.0% to about 20.0% (e.g., 10.0%), farnesol in an amount ranging from about 0.1% to about 1.0% (e.g., 0.5%), fragrance (for example citrus fragrance) in an amount ranging from about 0.01 to about 0.10% (e.g., 0.05%), and cosmocil CQ (comprising water and polyaminopropyl biguanide) in an amount ranging from about 0.01% to about 0.5% (e.g., 0.05%).

In several embodiments, a non-persistent foaming soap is provided comprising (by weight of the formulation) deionized water in an amount ranging from about 60% to about 70% (e.g., 68.58%), butylene glycol in an amount ranging from about 0.5% to about 2.0% (e.g., 1.0%), citric acid in an amount ranging from about 0.1% to about 1.0% (e.g., 0.6%), zinc gluconate in an amount ranging from about 0.1% to about 1.0% (e.g., 0.3%), benzethonium chloride in an amount ranging from about 0.05% to about 1.0% (e.g., 0.2%), mackamine LO (comprising water and lauramine oxide) in an amount ranging from about 5.0% to about 10.0% (e.g., 8.0%), caltaine C-35 (comprising water cocamiopropyl betaine, and sodium chloride) in an amount ranging from about 5.0% to about 10.0% (e.g., 7.0%), carsoquat CT-429 (comprising water and cetrimonium chloride) in an amount ranging from about 3.0% to about 10.0% (e.g., 5.0%), lauramide DEA in an amount ranging from about 0.5% to about 2.0% (e.g., 1.1%), PPG-2 hydroxyethyl cocamide in an amount ranging from about 1.0% to about 5.0% (e.g., 3.0%), methylchloroisothiazolinone in an amount ranging from about 0.01% to about 1.0% (e.g., 0.07%), actiphyte of aloe vera (comprising glycerin, water aloe barbadensis leaf extract) in an amount ranging from about 0.05% to about 1.0% (e.g., 0.1%), 200 proof alcohol in an amount ranging from about 2.0% to about 20.0% (e.g., 5.0%), and fragrance (for example natural fragrances, such as a menthol, lavender or citrus fragrance) in an amount ranging from about 0.01 to about 0.10% (e.g., 0.05%). In one embodiment, the fragrance contributes to the antimicrobial properties and/or other desirable effect In several embodiments, the formulation is suitable for application to a surface is infected gram-positive and gram-negative bacteria and/or a plurality of microbes, such as for example human or animal skin or an inorganic surface.

In several embodiments, the terpene is present in the topical formulation in an amount ranging from about 0.25% to about 0.60% by weight of the formulation. In several embodiments, the terpene or derivative thereof comprises farnesol. In some embodiments, another terpenoid or derivative thereof is used in addition to, or in place of farnesol. In several embodiments, tocopheryl acetate is present in the topical formulation in an amount ranging from about 0.05% to about 0.5% by weight of the formulation. In several embodiments, polyaminopropyl biguanide is present in an amount ranging from about 0.05% to about 0.20% by weight of the formulation. In several embodiments, the quaternary ammonium salt comprises benzethonium chloride.

In several embodiments, the formulation further comprises alcohol in an amount ranging from about 8% to about 20% by weight of the formulation. Additionally, in several embodiments, the topical formulation further comprises chlorhexidine gluconate in an amount ranging from about 0.10% to about 0.40% by weight of the formulation. In some embodiments, the formulation further comprises hydroxyethyl ethylcellulose in an amount ranging from about 0.05% to about 0.20% by weight of the formulation. In several embodiments, the formulation further comprises one or more zinc salts in an amount ranging from about 0.05% to about 0.60% by weight of the formulation. In some embodiments, the one or more zinc salts comprises zinc lactate, zinc gluconate, combinations thereof, and/or a zinc matrix. In several embodiments, the formulation further comprises panthenol in an amount ranging from about 0.25% to about 0.60% by weight of the formulation.

In several embodiments, the formulation further comprises one or more additional emollient compounds. In several embodiments, the formulation further comprises one or more of Vitamins A, B, K, and C. In some embodiments, the formulation further comprises an essential oil. In some embodiments, the essential oil comprises eucalyptus oil. In several embodiments, the eucalyptus oil is present in an amount ranging from about 0.05% to about 0.5% by weight of the formulation. Other oils may be used, depending on the embodiment. In some embodiments, combinations of oils are used, either alone or in combination with a fragrance, in order to provide a desirable scent or odor to the formulation.

In several embodiments, the dual action antimicrobial effects are achieved by dispensing between about 0.1 and 0.8 mL of the formulation onto a surface infected with gram-positive and gram-negative bacteria and/or a plurality of microbes. In several embodiments, the amount required to achieve immediate and/or persistent effects is on the lower end of the range. This is advantageous in several embodiments, because this increases the usability of the formulation (e.g., a wider range of users can correctly use the product, such as small children, individuals with limited flexibility, etc.). In some embodiments, the larger volumes are advantageous, however, as they allow complete coverage of certain surfaces (e.g., a surgical surface or equipment). In conjunction with the viscosities of the formulations disclosed herein, achieving highly effective, broad spectrum antimicrobial effects is more easily achieved in several embodiments. While multiple doses are desired in some embodiments, in several embodiments, the immediate and/or the persistent antimicrobial effects are achieved using a single dose of the formulation. In some embodiments, healthy microbes (e.g., good bacteria) are unaffected or less affected by some of the formulations described herein.

In several embodiments, there is also provided a kit comprising one or more of the formulations disclosed herein as well as instructions for use of the particular formulation. In some embodiments, kits may comprise applicators.

DETAILED DESCRIPTION

Figure 1:
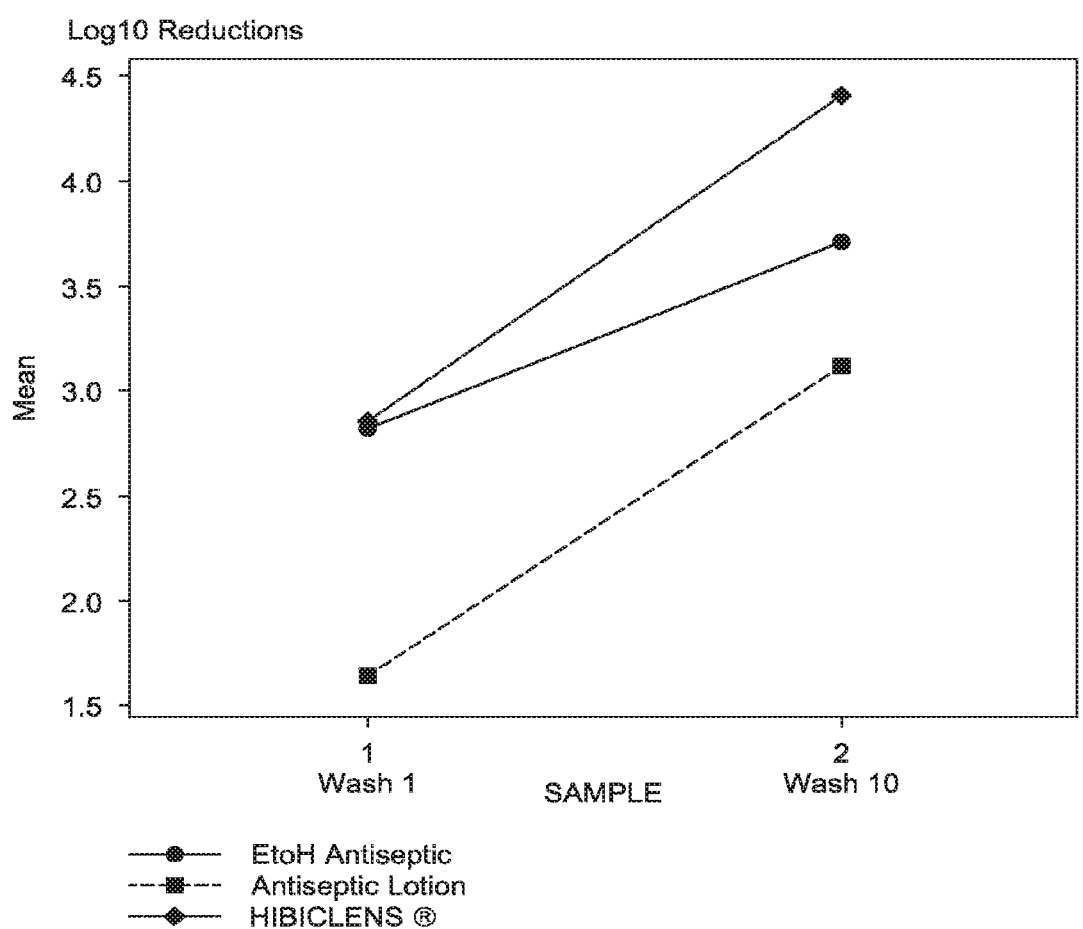
FIG. 1 depicts data comparing the antimicrobial effectiveness of various sanitizing formulations after multiple re-infections with *S. marcescens* and multiple applications of the formulations.

Hospitals, ambulances, emergency treatment settings, workplace environments, public places and even household settings are linked by the ever-present threat of microorganisms, and the possibility of developing and propagating an infection, disease or other illness. As can be appreciated by simply viewing historical data from the Centers for Disease Control (CDC) depicting the spread of the flu virus over several past years, the rate and breadth to which an illness can spread is surprising. This is largely due to, at least in some part, the ease with which certain microorganisms can be spread. By way of example, those infected with a respiratory virus, for example, (who may not yet show overt symptoms of the infection) can spread the virus up to a distance of about 6 feet. With respect to the flu virus (and other microorganisms) spreading can be due to virus-containing droplets formed when infected individuals cough, sneeze or talk. These droplets can unknowingly be inhaled by people who are nearby or ingested by touching a surface or object that has flu virus on it and then touching their own mouth or nose. Given that the number of people or surfaces an infected individual could come into contact with on a daily basis (for example riding a public bus on the way to work or out to lunch), the potential for spreading of microorganism-borne illnesses is vast.

For example, according to the CDC, from 1976 to 2006, estimates of influenza-associated deaths in the United States alone range from a low of about 3,000 to a high of about 49,000 people. On average, more than 200,000 people are hospitalized in the United States each year due to complications related to seasonal influenza. The immune systems of healthy individuals often successfully combat such microorganism-borne illnesses, but even healthy individuals can be at heightened risk. Elderly, those who are already sick or otherwise immune-compromised, and children are also at risk, and perhaps even more severe outcomes. Thus, when expanded to other microorganism-borne illnesses and considering the various at-risk populations (especially those in less developed regions that lack ready access to clean water and soaps), the potential for increased health care costs (which of course can lead to a feed-forward spread of an illness), lost business or personal revenue, reduced education time and productivity, and other effects, there is a need to provide formulations and methods that can reduce and/or eliminate a wide variety of microorganisms on both a short and long-term basis. The formulations and methods presented herein address this need by providing wide-spectrum antimicrobial formulations and methods for using the same to effect both short term and persistent antimicrobial effects. Several embodiments are particularly advantageous because they do not contribute to bacterial resistance to antibiotics.

Infections and Microorganisms

As discussed above, the potential spread of microorganisms and the associated illnesses and infections are large. There are a variety of different types or microorganism-based infections or illnesses. A major source of illness is hospital acquired infections or health-care associated infections. Once in a hospital, it is only a few hours until a patient's own microbial flora begin to acquire characteristics of the surrounding pool of microorganisms. An infection that become clinically evident after 48 hours of hospitalization can be considered hospital-acquired, while those developing after the patient is discharged from the hospital can be considered healthcare-associated (if the organisms were acquired during the hospital stay). Use of the formulations disclosed herein, alone or in conjunction with infection surveillance programs can, in several embodiments, significantly reduce hospital-acquired and healthcare-associated infections. Moreover, their use can also allow better prioritization of resources and efforts to improving medical care.

Other environments present opportunities for spread of microorganisms and associated illnesses. Non-limiting examples include, dental offices, specialty surgical suites, physician offices, care-provided homes, or other medical care facilities, emergency vehicles (e.g., ambulances or fire engines), restaurants, food preparation areas (e.g., butcher shops, grocery stores), public or private transportation vehicles or venues, schools, playgrounds, sports or exercise venues, residential housing (e.g., dormitories, hostels, or hotels), etc. In several embodiments, the user (e.g., a non-medical professional) applies the formulation(s) to a surface susceptible to microorganism contamination (e.g., a user can apply the formulation to his/her own skin).

As used herein, the term "microorganism" shall be given its ordinary meaning and shall include, but not be limited to, viruses (including but not limited to human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, and the like), prions, parasites, fungi, mold, yeast and bacteria (both gram-positive and gram-negative) including, among others, *Candida albicans, Aspergillus niger, Escherichia coli* (*E. coli*), *Pseudomonas aeruginosa* (*P. aeruginosa*), and *Staphylococcus aureus* (*S. aureus*), Group A streptococci, *S. pneumoniae, Mycobacterium tuberculosis, Campylobacter jejuni, Salmonella, Shigella*, and a variety of drug resistant bacteria. The terms microorganism and microbe shall be used interchangeably. Microbes can include wild-type, genetically-engineered or modified organisms. In several embodiments, the formulations and methods disclosed herein are for topical use or treatment of a surface. However, in some embodiments, other uses or treatments are used to achieve antimicrobial effects.

Antimicrobial Effects

The formulations and methods disclosed herein provide a variety of antimicrobial effects. As used herein, the term "antimicrobial" shall be given its ordinary meaning, and shall also refer to a substance compound or formulation that kills or inhibits and/or otherwise reduces the number, growth or activity of microorganisms. It has been established that hand washing is often incomplete, and that washing with non-antimicrobial soap leaves no persistent effect. The formulations provided herein result in substantially greater reduction (both short and long-term) of a target microorganism population than can be achieved through the use of plain soap. This translates to, in several embodiments, a reduced risk of disease acquisition and/or organism transmission. In several embodiments, the formulations reduce the risk of skin infection due to one's own resident skin flora and/or the acquisition of illness due to transmission of transient organisms from oneself or from others via various transmission routes. In several embodiments, the formulations are also used to facilitate wound healing (e.g., by reducing or preventing infection with one or more microorganisms). In several embodiments, the formulations are used to treat acne. In several embodiments, the formulations disclosed herein moisturize the skin in addition to reducing acne, but have limited side effects (e.g., are without drying effects on the skin). In several embodiments, fungal infections can be treated and/or prevented by application of the formulations disclosed herein.

In some embodiments, the formulations kill the microorganisms (e.g., they act as microbiocidal agents). In several embodiments, the formulations kill greater than 50% of the microorganisms contacted by the formulation. In some embodiments, greater kill rates are achieved, for example, greater than 60%, greater than 70%, greater than 80%, greater than 85%, greater than 90%, greater than 91%, greater than 92%, greater than 93%, greater than 94%, greater than 95%, greater than 96%, greater than 97%, greater than 98%, greater than 99%, greater than 99.9%, and overlapping ranges thereof. In several embodiments, the formulations provide a complete kill of the microorganisms (e.g., 100%). In several embodiments, a kill rate is achieved that substantially reduces the transmission or spread of the microorganism from person to person (or person to surface, or surface to surface). In some embodiments, the number of microorganisms is substantially reduced after contact with the formulations as provided herein. For example, in some embodiments, a reduction in microorganism number of about 2 log is achieved. In other embodiments, greater log reductions are achieved, for example, about 2.5 log reduction, about 2.8 log reduction, about 3.0 log reduction, about 3.2 log reduction, about 3.5 log reduction, about 4.0 log reduction, about 5.0 log reduction, and overlapping ranges thereof.

In some embodiments, formulations and methods provided herein, inhibit the microorganisms (e.g., they act as microbiostatic agents). In some embodiments, the inhibition is of the growth and/or reproduction, function, metabolism, and/or activity of the microorganisms. In some embodiments, the microorganisms are inhibited by 50% or more. In some embodiments, greater degrees of inhibition are achieved, for example, greater than 60%, greater than 70%, greater than 80%, greater than 85%, greater than 90%, greater than 91%, greater than 92%, greater than 93%, greater than 94%, greater than 95%, greater than 96%, greater than 97%, greater than 98%, greater than 99%, greater than 99.9%, and overlapping ranges thereof. In several embodiments, the formulations provide a complete kill of the microorganisms (e.g., 100%). In some embodiments, the inhibition is sufficient to cause the microorganism to no longer be infectious; however, the microorganism is not necessarily dead. In other embodiments, the inhibition (either directly or indirectly) leads to the death of the microorganism.

There exist a variety of antimicrobial formulations that kill only certain, limited, microbial populations. Thus, such formulations are not suitable for killing a wide variety of microorganisms, but rather have limited efficacy, and therefore limited suitability for applications in which a wide variety of microorganisms may be present. Moreover, some such formulations are less preferred because of various possible side effects, including but not limited to, drying of the skin, residue post-application, skin irritation, skin rash development. These side effects, among others, can be exacerbated by frequent use, as may be required in certain microorganism-rich environments.

The formulations disclosed herein, in several embodiments, function as broad-spectrum antimicrobials. As such, the formulations disclosed herein kill or inhibit multiple different kinds of microorganisms, when present, either alone or in combination with one another. The formulations disclosed herein are particularly advantageous, in some embodiments, because they are effective against microorganisms that are relatively easy to kill, as well as those organisms that are more difficult to kill. The formulations disclosed herein are, in several embodiments, effective at killing or inhibiting both gram-positive and gram-negative bacteria, drug-resistant bacteria, viruses, fungi, mold, yeasts, parasites, prions, as well as the other microorganisms disclosed herein, or combinations thereof. This broad-spectrum efficacy allows for, in some embodiments, a single formulation to be used to effectively kill (or otherwise inhibit) these widely differing types of microorganisms. As a result, transmission of these microorganisms (e.g., from person-to-person or surface to surface) is reduced, thereby reducing or preventing spread of microorganisms. Existing formulations, in contrast, may only be effective against only one or just a few of these types of microorganisms. As a result, transmission of some microorganisms should be reduced and transmission of others would be unaffected. In certain microorganism rich environments, in particular those with individuals susceptible to infection, such as hospitals or other health care facilities, existing formulations would thus be less desirable due to their lesser efficacy. In contrast, the formulations disclosed herein in several embodiments, with their broad-spectrum antimicrobial effects would provide substantially more benefit in such environments do to the reduction and/or prevention of transmission of the wider spectrum of microorganisms.

Moreover, in several embodiments, the formulations disclosed herein provide a multiphase antimicrobial effect. As discussed herein, the formulations have both a short-term and a long-term (e.g., persistent) antimicrobial effect. The short-term effect, in several embodiments provides a rapid and robust inhibition or kill of microorganisms, which therefore results in a reduced possibility of transmission on a short-term basis because of the substantial reduction in microorganism numbers shortly after contact with the formulation. In some embodiments, the short-term effect occurs within a timeframe of several seconds up to about several minutes. In several embodiments, the formulations disclosed herein provide extended antimicrobial effects, e.g., about 10 minutes, about 15 minutes, about 25 minutes, about 35 minutes, and ranges therebetween. In several embodiments, in addition to the short-term and intermediate effects, the long-term (e.g., persistent) effects function to inhibit or kill microorganisms on a longer timescale, for example, on the order of hours.

In several embodiments, the timeframe in which killing or inhibition of the microorganism is achieved is a short-term timeframe. In several embodiments, killing or inhibition of the microorganisms is instantaneous (e.g., inhibition or death of the microorganism occurs as soon as the formulation context, the microorganism). In some embodiments, killing or inhibition occurs within about 2 seconds, within about 5 seconds, within about 7 seconds, within about 10 seconds, within about 15 seconds, within about 20 seconds, or within times in between the timeframes listed above. For example, in some embodiments, substantial (or complete) inhibition or kill of microorganisms occurs within about 10 to about 15 seconds, about 15 seconds to about 20 seconds, about 20 seconds to about 30 seconds, about 30 seconds to about 40 seconds, about 40 seconds to about 60 seconds, about 60 seconds to about 90 seconds, about 90 seconds to about 120 seconds, and overlapping ranges thereof. In some embodiments, the short-term effect persists for several minutes, for example, about 1 minute to about 2 minutes, about 2 minutes to about 3 minutes, about 3 minutes to about 4 minutes, about 4 minutes to about 5 minutes, about 5 minutes to about 15 minutes, about 15 minutes about 30 minutes, about 35 minutes, about 40 minutes, about 45 minutes, and overlapping ranges thereof. In several embodiments, the short term killing of microorganisms is particularly advantageous because the microbial load is substantially or completely reduced prior to the point in time at which the microorganisms could spread. In several embodiments, the rapid kill of microorganisms prevents the spread of the microorganisms which reduces the risk of transmission of the microorganism from a first subject to a second subject. In conjunction with this effect, the rapid kill also reduces the risk and/or severity of infection that may be suffered by the first subject as a result of the microorganisms (e.g., the fewer the microorganisms present on the first subject, the less severe any resulting infection is). Thus, not only do the formulations and methods disclosed herein serve to reduce the spread of infectious microorganisms (which reduces the number of individuals infected by the microorganisms) it also serves to reduce the impact of the remaining (if any) microorganisms on a particular subject. In several embodiments, the rapid effect results in kill rates of greater than 90%, greater than 91%, greater than 92%, greater than 93%, greater than 94%, greater than 95%, greater than 96%, greater than 97%, greater than 98%, greater than 99%, greater than 99.9%, and overlapping ranges thereof. In several embodiments, the rapid effect results in complete kill of the microorganisms (e.g., 100%).

For example, the formulations and methods disclosed herein provide a persistent effect resulting in substantial (or complete) inhibition or kill of microorganisms for timeframe ranging from, for example, about 20 to about 40 minutes (e.g., about 35 minutes), about 40 to about 60 minutes, about 60 to about 90 minutes, about 90 to about 120 minutes, about 120 to about 150 minutes, about 150 to about 180 minutes, about 180 to about 240 minutes, and overlapping ranges thereof. In several embodiments, the persistent effect of the formulations disclosed herein results for longer periods of time, ranging from about 30 min. to about one hour, about one hour to about two hours, about two hours to about three hours, about three hours to about four hours, about four hours to about six hours, about six hours to about eight hours, about eight hours to about 12 hours, and overlapping ranges thereof. In some embodiments, certain formulations provide an even more extended persistent effect, such as from about four hours to about six hours, about six hours to about eight hours, about eight hours to about 12 hours, and overlapping ranges thereof. In several embodiments, the persistent effect achieves kill rates greater than 70%, greater than 80%, greater than 85%, greater than 90%, greater than 91%, greater than 92%, greater than 93%, greater than 94%, greater than 95%, greater than 96%, greater than 97%, greater than 98%, greater than 99%, greater than 99.9%, and overlapping ranges thereof. In several embodiments, the persistent effect complete kill of the microorganisms (e.g., 100%).

Advantageously, in several embodiments, the combined rapid effect and persistent effect of the formulations disclosed herein reduces the microorganism load in two important phases. First, the microbial load is reduced on a short-term basis, providing a significantly reduced degree of initial spread of the microorganisms (e.g., from subject to subject, from subject to surface, etc.) and second, on a longer-term basis, which further reduces the spread of the microorganisms, especially in conjunction with other sanitary practices (e.g., hand washing). The quick initial kill is particularly advantageous because the formulations actively kill the microorganisms prior to a time within which an individual could engage in some other antimicrobial practice, for example, washing hands. The persistent effect supplements the quick kill, and further reduces risk of later disease acquisition or transmission of microorganisms.

Antimicrobial Formulations

There are provided for herein a variety of different types of antimicrobial formulations in different forms. In several embodiments, the antimicrobial formulations are formulated as a hand wash or surgical scrub. In several embodiments, such formulations are foaming. In several embodiments, the foam generated is sufficiently thick to reduce run-off of the formulation during use. In several embodiments, the anti-microbial formulations are formulated as a soap (either bar soap or liquid/gel soap). In several embodiments the anti-microbial formulations are formulated as a spray (e.g., an aerosol) or a gel. Non-gel sanitizers are provided in several embodiments. In several embodiments, the antimicrobial formulations are formulated as a lotion or other liquid form. In some embodiments, the formulations are provided as a cream or thickened lotion. In several embodiments, the formulations can be incorporated into other products, including but not limited to, cosmetics, body wash, shampoo, conditioner, sunscreens, insect repellants, and the like.

In several embodiments, the formulations are formulated as, or incorporated into, anti-bacterial soap, liquid soap, bar soap, bath soaps, cosmetic sunscreen preparations, deodorant for personal use, hair care preparations, hair conditioners, hair shampoo, hand lotions, hand scrubs, hand soaps, non-medicated acne treatment preparations, non-medicated dental products and rinses (e.g., anti-plaque/anti-tartar formulations toothpaste, dental floss), acne treatment preparations, hand-sanitizing preparations, medicated dental products and rinses (e.g., anti-plaque/anti-tartar formulations, toothpaste, dental floss), medicated hair care preparations, medicated hand wash, medicated lotions for skin, medicated sunscreen, household deodorizer, cleaning agents and preparations, cleaning preparations for cleaning surfaces, disinfectant soaps, all-purpose disinfectants, anti-microbial hand-wash, antibacterial hand lotions, antibacterial spray, antimicrobial coatings to treat the growth of mold, mildew, bacteria and fungus on various surfaces, adhesive bandages, antiseptic wipes, antiseptics, bandages for skin wounds, bandages impregnated with antiseptic, first aid kits, fungal medications, fungicides, gauze, germicides, gloves for medical use, surgical caps, surgical drapes, surgical gowns, surgical masks, surgical scrub suits, surgical shoe covers, surgical devices and instruments, surgical sponges, sanitizing preparations for hospital use, sanitizing preparations for household use, sanitizing preparations for use in institutional and industrial areas, sanitizing wipes, virucides and the like.

In several embodiments the formulations comprise an alcohol. In several embodiments, denatured alcohol is used. In several embodiments, the alcohol is about 200 proof, while in other embodiments, lesser proof alcohol is used (e.g., 40, 80, 100 proof). Alcohols include, but are not limited to methanol, ethanol, isopropyl alcohol, butyl alcohol, pentanol, hexadecan-1-ol, ethane-1,2-diol, propane-1,2,3-triol, butane-1,2,3,4-tetraol, pentane-1,2,3,4,5-pentol, hexane-1,2,3,4,5,6-hexol, heptane-1,2,3,4,5,6,7-heptol, prop-2-ene-1-ol, 3,7-dimethylocta-2,6-dien-1-ol, c3h3ohprop-2-in-1-ol, cyclohexane-1,2,3,4,5,6-hexol, and 2-(2-propyl)-5-methyl-cyclohexane-1-ol. In several embodiments, the alcohol functions as an active killing agent, while in some embodiments, the alcohol is non-active. In several embodiments, the alcohol works synergistically with one or more additional ingredients to provide the antimicrobial effects of the formulations. In several embodiments, the alcohol provides, at least in part, the rapid kill of microorganisms upon contact (or soon thereafter) with the microorganisms. In some embodiments, the alcohol also contributes, at least in part, to the persistent effect of the formulations. Depending on the formulation, the amount of alcohol on a percent weight basis ranges from about 5% to about 75%. In several embodiments, the amount of alcohol ranges from about 5% to about 7%, about 7% to about 10%, about 10% to about 12%, about 12% to about 14%, about 14% to about 16%, about 16% to about 20%, and overlapping ranges thereof. In some embodiments, the amount of alcohol ranges from about 12% to about 16%, including about 12% to about 13%, about 13% to about 13.5%, about 13.5% to about 14%, about 14% to about 14.5%, about 14.5% to about 15%, bout 15% to about 15.5%, about 15.5% to about 16%, and overlapping ranges thereof. In some embodiments, greater amounts of alcohol are used, for example, about 20% to about 40%, about 40% to about 60%, about 60% to about 65%, about 65% to about 67%, about 67% to about 69%, about 69% to about 72%, about 72% to about 75% and overlapping ranges thereof. In some embodiments, the formulations are alcohol free. In several embodiments, the formulations comprise less than about 20% alcohol, e.g., less than about 15%, less than about 10%, less than about 5% or ranges therebetween.

In several embodiments, in addition to or in place of alcohol, chemical agents are used to provide antimicrobial effects. In several embodiments, chlorhexidine is used, and represents a non-limiting example of a chemical antimicrobial agent. Chlorhexidine is particularly suited for providing antibacterial effects, against both gram-positive and gram-negative bacteria, though it provides additional antimicrobial effects as well. In several embodiments, chlorhexidine, or other chemical agent provides, at least in part, the immediate antimicrobial effect of the formulation. In some embodiments, the chlorhexidine works in conjunction with one or more additional component of the formulation, such as, for example, alcohol, to provide the immediate effect. In some embodiments, however, chlorhexidine also contributes, at least in part, to the persistent effect of certain formulations. Various salts of chlorhexidine are used, depending on the embodiment. Non-limiting examples include chlorhexidine digluconate, chlorhexidine diacetate, chlorhexidine phosphanilate, and chlorhexidine dihydrochloride. Combinations of the various salts, or the chlorhexidine base are used in still additional embodiments. In several embodiments, the amount of chlorhexidine (or other chemical antimicrobial; on a % weight basis) ranges from about 0.01% to about 2%, including about 0.01% to about 0.05%, about 0.05% to about 0.075%, about 0.075% to about 0.10%, about 0.10% to about 0.15%, about 0.15% to about 0.175%, about 0.175%, to about 0.19%, about 0.19% to about 0.20%, about 0.20% to about 0.22%, about 0.22% to about 0.25%, about 0.25% to about 0.30%, about 0.30% to about 0.50%, about 0.50% to about 1.0%, about 1.0% to about 1.5%, about 1.5% to about 2.0%, about 2.0% to about 3.0%, and overlapping ranges thereof. In certain formulations, surprisingly antimicrobial effects are achieved even though the amount of the chemical antimicrobial is below the "active kill" level as currently recognized by the FDA (e.g., 0.4 for chlorhexidine). In some embodiments, the formulations are free of chemical antimicrobials. For example, some embodiments of the formulations are chlorhexidine free.

In several embodiments, the formulations comprise one or more quaternary ammonium compounds. In some embodiments, the quaternary ammonium compounds are synthetic, while in other embodiments, they are naturally occurring. In some embodiments, synthetic quaternary ammonium compounds comprising long alkyl chains are preferred, though those with short alkyl chains are optionally used. In several embodiments, the quaternary ammonium compounds provide and/or supplement the persistent kill effect of the formulation. Non-limiting examples of quaternary ammonium compounds include benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, and domiphen bromide, or combinations of two or more thereof. In several embodiments, the quaternary ammonium compounds provide potent antimicrobial effects by disrupting the cell membrane of microorganisms. In some embodiments, this disruption is sufficient to kill or inhibit the microorganism, while in some embodiments, the disruption provides a route by which another agent in the formulation provides the killing or inhibiting effect. In several embodiments, the amount of quaternary ammonium compound (on a % weight basis) ranges from about 0.001% to about 2%, including about 0.001% to about 0.005%, about 0.005% to about 0.075%, about 0.075% to about 0.01%, about 0.01% to about 0.02%, about 0.02% to about 0.03%, about 0.03% to about 0.04%, about 0.04% to about 0.05%, about 0.05% to about 0.075%, about 0.075% to about 0.10%, about 0.10% to about 0.11%, about 0.11% to about 0.12%, about 0.12% to about 0.13%, about 0.13% to about 0.14%, about 0.14% to about 0.15%, about 0.15% to about 0.175%, about 0.175% to about 0.19%, about 0.19% to about 0.20%, about 0.20% to about 0.22%, about 0.22% to about 0.25%, about 0.25% to about 0.30%, about 0.30% to about 0.40%, about 0.40% to about 0.50%, about 0.50% to about 1.0%, about 1.0% to about 1.5%, about 1.5% to about 2.0%, about 2.0% to about 3.0%, and overlapping ranges thereof. In several embodiments, combinations of quaternary ammonium compounds are used. In certain such embodiments, the total amount of the quaternary ammonium compounds (on a per weight basis) is as described above. In other embodiments, the amounts listed above are for each individual quaternary ammonium compound. In some embodiments, the formulations are free of quaternary ammonium compounds or salts thereof.

In several embodiments, the antimicrobial efficacy of the quaternary ammonium compounds is pH dependent. Thus, in some embodiments, the pH of the formulation is adjusted to be within a certain range to improve the function of the quaternary ammonium compounds. For example, in some embodiments, the formulations range in pH from about 3.5 to about 4.0, about 4.0 to about 4.5, about 4.5 to about 5.5, about 5.5 to about 6.0, about 6.0 to about 6.5, about 6.0 to about 6.5, and overlapping ranges thereof. In several embodiments, the pH is more alkaline.

In several embodiments, certain ingredients in the formulation supplement the antimicrobial efficacy of the formulation. In some embodiments, this supplementation is realized by making an active killing agent more effective as an antimicrobial while in some embodiments, the additional ingredients also function as killing agents. In some embodiments, the supplementation is realized by virtue of a disinhibition of one or more other components of the formulation. In some embodiments, the alternative killing ingredient supplements the overall function of the formulation because of a different mechanism of action. In some embodiments, the formulation comprises a single active ingredient. In several embodiments, the presence of one or more ingredients potentiates the efficacy of one or more other ingredients either through a synergistic mechanistic action, and/or by virtue of reducing an inhibitory effect on another ingredient. For example, depending on the embodiment, certain components of the formulations disclosed herein are pH sensitive, in that their function is greater when the formulation is within a certain pH range. In some embodiments, the additional components of the formulation are present to maintain the pH within that desired range, thereby improving the function of the first component.

In several embodiments, the formulation comprises one or more terpenes or derivatives thereof. In several embodiments, the terpenes are hemiterpenes (e.g., prenol or isovaleric acid), monoterpenes (e.g., geraniol, limonene and terpineol), sesquiterpenes (e.g., farnesenes, farnesol), diterpenes (e.g., cafestol, kahweol, cembrene and taxadiene, sesterterpenes (e.g., geranylfarnesol), triterpenes (e.g., squaline, lanosterol, or cycloartenol), sesquarterpenes (e.g., ferrugicadiol and tetraprenylcurcumene), tetraterpenes (e.g., lycopene, carotenes), or polyterpenes. Combinations of the various types of terpenes (or derivatives) may be used, in several embodiments. In some embodiments, the terpenes provide additional antimicrobial effects. In some embodiments, the terpenes contribute to the overall efficacy of the formulation by increasing the breadth of microorganisms that the formulation is effective against (e.g., increases in the kill spectrum). In some embodiments, the terpenes contribute to the persistent effect of the formulation. However, in some embodiments, the terpenes contribute to the rapid kill effect of the formulation. Additionally, in some embodiments, the terpenes function to buffer the pH of the formulation (by virtue of, at least in part, the anionic charge of the terpene). In some embodiments, this buffering capacity aids in the stability of the formulation, or in some embodiments in the process of manufacturing the formulation. In still additional embodiments, the buffered pH is leads to a reduced skin irritant potential of the formulation. In several embodiments the buffered pH improves or potentiates the antimicrobial efficacy of one or more other components of the formulation. In several embodiments, the anionic nature of the terpene allows buffering of other cations (in addition to or in place of H+, as discussed above) which contributes to the ionic stability of the formulation as a whole.

In several embodiments, the formulation comprises a terpene (or derivative thereof) in an amount ranging (on a % weight basis) between about 0.1% to about 2%, including about 0.1% to about 0.2%, about 0.2% to about 0.3%, about 0.3% to about 0.4%, about 0.4% to about 0.45%, about 0.45% to about 0.5%, about 0.5% to about 0.55%, about 0.55% to about 0.6%, about 0.6% to about 0.65%, about 0.65% to about 0.7%, about 0.7% to about 1%, about 1% to about 1.5%, about 1.5% to about 2%, and overlapping ranges thereof. In some embodiments, the formulations are free of terpenes or derivatives thereof.

In addition, several embodiments of the formulation comprise vitamins or analogs thereof. In several embodiments, the formulation comprises panthenol, an alcohol analog of vitamin B5. In some embodiments, panthenol functions as an emollient and/or as a moisturizer. As discussed above, in several embodiments, panthenol contributes to the pH of the formulation. In several embodiments, panthenol supplements the overall antimicrobial efficacy of the formulation in a synergistic fashion. In several embodiments, panthenol is provided as a racemic mixture of D- and L-panthenol, while in some embodiments, the formulation comprises only one of the two enantiomers. In several embodiments, the formulation comprises panthenol in an amount ranging (on a % weight basis) between about 0.1% to about 2%, including about 0.1% to about 0.2%, about 0.2% to about 0.3%, about 0.3% to about 0.4%, about 0.4% to about 0.45%, about 0.45% to about 0.5%, about 0.5% to about 0.55%, about 0.55% to about 0.6%, about 0.6% to about 0.65%, about 0.65% to about 0.7%, about 0.7% to about 1%, about 1% to about 1.5%, about 1.5% to about 2%, and overlapping ranges thereof. In some embodiments, the formulations are panthenol free.

In several embodiments, the formulation comprises one or more biguanide polymers, oligomers, or biguanides. For example, in some embodiments, the formulation comprises polyaminopropyl biguanide, which imparts bactericidal and/or fungicidal effects to the formulation (among other effects, depending on the amount used in the formulation). In some embodiments, the polymer strands are disruptive to the integrity of the membranes of certain microorganisms, which leads to lethal effects for the microorganisms. Additionally, polyaminopropyl biguanide, in several embodiments, can induce lethal DNA damage in the microorganism. Advantageously, the greater degree of complexity of the cell membrane of higher species, such as humans, reduces the potential adverse effects of the polyaminopropyl biguanide on the cells of the higher species. Thus, polyaminopropyl biguanide, in several embodiments specifically targets microorganisms. Advantageously, this preference for action on less complex cell types also reduces the potential for dermal irritation resulting from use of the formulations. In some embodiments, polyaminopropyl biguanide is provided as a mixture of various length polymers, and as such, the various lengths provide various efficacies against certain types of microorganisms, increasing the spectrum of possible antimicrobial kills. In several embodiments, polyaminopropyl biguanide, or other biguanides, contribute, at least in part, to the immediate antimicrobial effect of the formulations. In several embodiments, polyaminopropyl biguanide, or other biguanides, contribute, at least in part, to the persistent antimicrobial effect of the formulations. In some embodiments, polyhexamethyl biguanide is used, either in addition to or in place of polyaminopropyl biguanide. In some embodiments, the formulations are free of biguanides. In several embodiments, polyaminopropyl biguanide is particularly advantageous because it is limited in its inhibitory effects on other components of the formulation. In several embodiments, the amount of polyaminopropyl biguanide, or other biguanide, (on a % weight basis) ranges from about 0.01% to about 3%, including about 0.01% to about 0.02%, about 0.02% to about 0.03%, about 0.03% to about 0.04%, about 0.04% to about 0.05%, about 0.05% to about 0.075%, about 0.075% to about 0.080%, about 0.080% to about 0.090%, about 0.090% to about 0.10%, about 0.10% to about 0.125%, about 0.125% to about 0.15%, about 0.15% to about 0.175%, about 0.19% to about 0.20%, about 0.20% to about 0.22%, about 0.22% to about 0.25%, about 0.25% to about 0.30%, about 0.30% to about 0.50%, about 0.50% to about 1.0%, about 1.0% to about 1.2%, about 1.2% to about 1.3%, about 1.3% to about 1.4%, about 1.4% to about 1.5%, about 1.5% to about 1.6%, about 1.6% to about 1.7%, about 1.7% to about 2.0%, about 2.0% to about 3.0%, and overlapping ranges thereof.

Several embodiments of the formulations comprise additional agents. These agents may contribute, at least in part, to the antimicrobial effect of the formulation (among other contributions). In some embodiments, the formulation comprises hydroxyethyl cellulose. In some embodiments, the hydroxyethyl cellulose comprises quaternized hydroxyethyl cellulose (also known as polyquaternium-10). In some embodiments, the formulation comprises hydroxyethyl ethylcellulose in addition to or in place of hydroxyethyl cellulose. In some embodiments, the formulations comprise a cellulose selected from the group consisting of calcium carboxymethyl cellulose, carboxymethyl cellulose acetate butyrate, carboxymethyl hydroxyethylcellulose, cellulose acetate, cellulose acetate butyrate, cellulose gum, cellulose acetate propionate, cellulose acetate propionate carboxylate, cellulose succinate, cetyl hydroxyethylcellulose, ethylcellulose, hydrolyzed cellulose gum, hydroxybutyl methylcellulose, hydroxyethylcellulose, hydroxyethyl ethylcellulose, hydroxypropylcellulose, hydroxypropyl methylcellulose, methylcellulose, hydroxypropyl methylcellulose acetate/succinate, methylcellulose, methyl ethylcellulose, methyl hydroxyethylcellulose, microcrystalline cellulose, potassium cellulose succinate, sodium cellulose sulfate, and combinations thereof. In some embodiments, the hydroxyethyl ethylcellulose (or other cellulose) works synergistically with other ingredients to produce the persistent kill effect of the formulation. In some embodiments, this synergism results, at least in part, from the limited inhibitory effect that the hydroxyethyl ethylcellulose has on other components of the formulation. In some embodiments, the hydroxyethyl ethylcellulose (or other cellulose) also functions as a thickening agent, thereby changing the viscosity of the formulation to a desired level, depending on the embodiment. In several such embodiments, the viscosity of the formulation contributes to its spreadability (e.g., surface area coverage), which in turn can impact the antimicrobial effect and/or use of the formulation. In several embodiments, the amount of hydroxyethyl ethylcellulose (or other cellulose) or other cellulose (on a % weight basis) ranges from about 0.001% to about 3%, including about 0.001% to about 0.005%, about 0.005% to about 0.0075%, about 0.075% to about 0.01%, about 0.01% to about 0.02%, about 0.02% to about 0.03%, about 0.03% to about 0.05%, about 0.05% to about 0.075%, about 0.075% to about 0.080%, about 0.080% to about 0.090%, about 0.090% to about 0.10%, about 0.10% to about 0.125%, about 0.125% to about 0.15%, about 0.15% to about 0.175%, about 0.19% to about 0.20%, about 0.20% to about 0.22%, about 0.22% to about 0.25%, about 0.25% to about 0.30%, about 0.30% to about 0.50%, about 0.50% to about 1.0%, about 1.0% to about 1.5%, about 1.5% to about 2.0%, about 2.0% to about 3.0%, and overlapping ranges thereof. In some embodiments, the formulations are free of one or all of cellulose, hydroxyethyl ethylcellulose, hydroxyethyl cellulose and/or quaternized hydroxyethyl cellulose. In several embodiments, the formulation further comprise lactic acid and/or lactate. Depending on the embodiment, the lactic acid and/or lactate is present in a total amount ranging from about 5% to about 15% (by weight), including about 5% to about 7%, about 7% to about 9%, about 9% to about 11%, about 11% to about 13%, about 13% to about 15%, and overlapping ranges thereof.

Several embodiments of the formulations disclosed herein employ multiple agents with complementary function, achieved by different mechanisms of action. For example, in some embodiments, the formulations comprise one or more zinc salts. The zinc salts can, in some embodiments, contribute to the immediate and/or persistent antimicrobial effect of the formulations and/or reduce the potential for dermal irritation resulting from use of the formulation. In some embodiments, zinc improves the feel of the formulation, e.g., the sensation of smoothness or silkiness when the formulation is used on a surface comprising skin and/or reduction in the stickiness of the formulation. In several embodiments, zinc also reduces the drying time of certain formulations. In several embodiments, the drying time of the formulation ranges from about 5 to about 30 seconds, including but not limited to about 5 to about 10 seconds, about 10 to about 15 seconds, about 15 to about 20 seconds, about 20 to about 25 seconds, about 25 to about 30 seconds, and overlapping ranges thereof. The zinc salts are water soluble in some embodiments, while in others water insoluble zinc salts are used. Combinations of water soluble and water insoluble may also be used, in certain embodiments. Non-limiting examples of zinc salts are zinc acetate, zinc butyrate, zinc gluconate, zinc glycerate, zinc glycolate, zinc formate, zinc lactate, zinc picolinate, zinc propionate, zinc salicylate, zinc tartrate, zinc undecylenate, zinc oxide, zinc stearate, zinc citrate, zinc phosphate, zinc carbonate, and zinc borate. In several embodiments the zinc is provided as a component of a zinc matrix. In some embodiments, one zinc salt is used, while in other embodiments, two or more zinc salts are used. In several embodiments, the amount of zinc salt (on a % weight basis) ranges from about 0.01% to about 2%, including about 0.01% to about 0.05%, about 0.05% to about 0.075%, about 0.075% to about 0.10%, about 0.10% to about 0.15%, about 0.15% to about 0.175%, about 0.175% to about 0.19%, about 0.19% to about 0.20%, about 0.20% to about 0.22%, about 0.22% to about 0.25%, about 0.25% to about 0.30%, about 0.30% to about 0.50%, about 0.50% to about 1.0%, about 1.0% to about 1.5%, about 1.5% to about 2.0%, about 2.0% to about 3.0%, and overlapping ranges thereof. In some embodiments, such as those employing more than one zinc salt, the total amount of all zinc salts (on a per weight basis) is as described above. Surprisingly, in some embodiments, lesser amounts of zinc in the formulation result in greater degrees of antimicrobial activity. In other embodiments, the amounts listed above are for each individual zinc salt in the formulation. In some embodiments, the formulations are free of zinc or zinc-containing matrices.

Several embodiments of the formulations disclosed herein employ one or more moisturizing or emollient agents. As used herein, the terms "moisturizer" and "emollient" shall be given their ordinary meaning, and shall be used interchangeably, and shall refer to agents that function to improve or maintain the hydration, softness, smoothness, and/or pliability of the skin and the like, in particular the epidermal layers. In some embodiments, the moisturizers function to help reduce dry skin, oily skin, aging skin (e.g., loss of elasticity), sensitive skin (e.g., eczema). In some embodiments, combinations of moisturizers are used, with each member of the combination providing complementary function to improve multiple aspects of the skin, for example, both dry and sensitive skin conditions are improved. In some embodiments, the moisturizing agents work as occlusives (e.g., they forming a thin film on the surface of the skin to prevent any loss of moisture). In some embodiments, the moisturizing agents work as humectants (e.g., they attract water from the air in order to moisturize the skin). In some embodiments, the moisturizing agents work to restore deficiencies in the skin (e.g., mineral, vitamins, lipids etc.). In some embodiments a single moisturizing agent can work with multiple mechanisms of action. In several embodiments, the moisturizer compounds comprise one or more of glycerin, dimethicone (including PEG-12 dimethicone). In several embodiments, such agents also improve tactile feel of the formulation.

In several embodiments the moisturizers are present in the formulation in an amount (on a % weight basis) ranging from about 0.5% to about 10%. In several embodiments, depending on the embodiment, the moisturizers are present in the formulation in an amount ranging from about 0.5% to about 1.0%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2.0%, about 2.0% to about 2.25%, about 2.25% to about 2.5%, about 2.5% to about 2.75%, about 2.75% to about 3.0%, about 3.0% to about 3.25%, about 3.25% to about 3.5%, about 3.5% to about 3.75%, about 3.75% to about 4.0%, about 4.0% to about 4.1%, about 4.1% to about 4.2%, about 4.2% to about 4.3%, about 4.3% to about 4.4%, about 4.4% to about 4.5%, about 4.5% to about 4.6%, about 4.6% to about 4.7%, about 4.7% to about 4.8%, about 4.8% to about 4.9%, about 4.9% to about 5.0%, about 5.0% to about 4.25%, about 5.25% to about 5.5%, about 5.5% to about 5.75%, about 5.75% to about 6.0%, about 6.0% to about 6.5%, about 6.5% to about 7.0%, about 7.0% to about 7.5%, about 7.5% to about 8.0%, about 8.0% to about 8.5%, about 8.5% to about 9.0%, about 9.0% to about 9.5%, about 9.5% to about 10.0%, and overlapping ranges thereof. In several embodiments, greater amounts of moisturizers are present in the formulation, such as, for example, about 10% to about 15%, about 15% to about 20%, about 20% to about 25%, about 25% to about 30%, about 30% to about 50%, and overlapping ranges thereof. In several embodiments, the formulations are free of moisturizer or emollient compounds.

In several embodiments, the formulations further comprise one or more vitamins and/or minerals. For example, in several embodiments, the formulations include, but are not limited to, one or more of vitamin E, A, K, C, B, and the like. In several embodiments, vitamins incorporated into the formulation function as antioxidants and/or reduce to production or deleterious effects of free radicals. In some embodiments, the vitamins induce a more rapid cellular "turn over", which results in a shorter time to bringing new cells to the surface of the skin, and as a result, a reduction in the rate of aging of the skin. In several embodiments, the vitamins induce capillary (or other small vessel) vasoconstriction, which results in a reduction in skin discoloration or other skin blemishes. In several embodiments, vitamins reduce the appearance of age spots and/or reduce discrepancies in the tone of various parts of the skin (e.g., result in a more uniform skin color). In some embodiments, vitamins also reduce the adverse skin effects associated with acne (e.g., skin reddening, scarring, discoloration, etc.). In several embodiments, the formulations are free of vitamins. In several embodiments, antimicrobial formulations for conditions such as acne or inflammatory skin conditions comprise an exfoliant. Exfoliants may be included in hand soaps and surgical scrubs. In some embodiments, formulations comprise a penetrant to enhance contact of the ingredients into the layers or pores of the skin.

Additional ingredients, depending on the embodiment include, but are not limited to, citric acid; foaming agents such as amine oxide surfactants (e.g., lauramine oxide); viscosity builders/foam stabilizers including but not limited to, lauramine oxide, cocamidopropyl betaine, disodium laureth sulfosuccinate, cocamidopropylamine oxide, lauramidopropyl betaine, lauramide DEA, methyl hydroxyethylcellulose (also known as Structure® CEL), stearamidopropyl dimethylamine); additional emollient agents such as, for example cetrimonium chloride, hydroxyethyl cocamide (which can also enable the fragrances to be solubilized, other oils and actives in certain formulation embodiments); compounds to maintain emulsions (e.g., prevent emulsion separation) such as, cetyl alcohol and/or cetearyl alcohol; preservative agents, including but not limited to, for example, methylchloroisothiazolinone, methylisothiazolinone (also known as Microcare® ITL), euxyl k 700 (benzyl alcohol, phenoxyethanol, potassium sorbate, and tocopherol) and the like; plant extracts, such as aloe extract, essential oils (including but not limited to volatile oil(s) obtained from a plant or an animal source comprising an active agent which may be, for example but not by way of limitation, a monoterpene or sesquiterpene hydrocarbon, alcohol, ester, ether, aldehyde, ketone, or oxide. Examples of these essential oils include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, and tangerine oil, or agents from the essential oils including but not limited to 1-citronellol, alpha-amylcinnamaldehyde, lyral, geraniol, farnesol, hydroxycitronellal, isoeugenol, eugenol, eucalyptus oil and eucalyptol, lemon oil, linalool, and citral) cocoa butter, and the like; fragrances including, but not limited to, floral, citrus, fruit, nut, vegetable, botanicals, woods, resin, mint, musk, spices, and the like; dimethicone; glycerine; conditioning agents/emulsifiers, such as Incroquat® Behnyl TMS (cetearyl alcohol, benhentrimonium methosulfate). Depending on the embodiments, such additional ingredients may be added alone or in combination, and in various amounts ranging from about 0.005% to about 10% (by weight), including about 0.005% to about 0.0075%, about 0.0075% to about 0.01%, about 0.01% to about 0.015%, about 0.015% to about 0.02%, about 0.02% to about 0.04%, about 0.04% to about 0.06%, about 0.06% to about 0.08%, about 0.08% to about 0.10%, about 0.10% to about 0.20%, about 0.20% to about 0.30%, about 0.30% to about 0.40%, about 0.40% to about 0.50%, about 0.50% to about 0.60%, about 0.60% to about 0.70%, about 0.70% to about 0.80%, about 0.80% to about 0.90%, about 0.90% to about 1.0%, about 1.0% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.7%, about 1.7% to about 1.8%, about 1.8% to about 1.9%, about 1.9% to about 2.0%, about 2.0% to about 2.25%, about 2.25% to about 2.5%, about 2.5% to about 2.75% about 2.75% to about 3.0% about 3.0% to about 3.25% about 3.25% to about 3.5% about 3.5% to about 3.75% about 3.75% to about 4.0% about 4.0% to about 4.25% about 4.25% to about 4.5% about 4.5% to about 4.75% about 4.75% to about 5.0% about 5.0% to about 5.5% about 5.5% to about 6.0% about 6.0% to about 6.5%, about 6.5% to about 7.0%, about 7.0% to about 7.5%, about 7.5% to about 8.0%, about 8.0% to about 8.5%, about 8.5% to about 9.0%, about 9.0% to about 9.5%, about 9.5% to about 10%, and overlapping ranges thereof. Some embodiments are free one or more of these additional ingredients.

Several embodiments of the formulations also comprise water (optionally deionized and/or distilled), which, depending on the embodiment, may be used to adjust the viscosity and/or feel of the formulation, solubilize one or more components of the formulation, adjust the pH, and/or finalize the concentrations of the formulation (bring the formulation to its final volume). Thus, water, in some embodiments is added in a range from about 1% to about 99% of the formulation, including from about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 99%, and overlapping ranges thereof.

In several embodiments, the formulation comprises at least one quaternary ammonium salt selected from the group consisting of benzethonium chloride and benzalkonium chloride. In several embodiments, the formulation comprises a terpene or derivative thereof and at least one quaternary ammonium salt selected from the group consisting of benzethonium chloride and benzalkonium chloride. Optionally, the formulations can further include one or more of zinc (e.g., a zinc salt), a chemical antimicrobial agent (e.g., chlorhexidine digluconate), a biguanide polymer (e.g., polyaminopropyl biguanide), a moisturizing agent (e.g., dimethicone), a viscosity builder/thickener (e.g., hydroxyethyl ethylcellulose), spreading agent (e.g., glycerine), a conditioning agent (e.g., a cationic conditioning agent such as incroquat), and/or alcohol. These formulations exhibit antimicrobial activity against one or more of the following microorganisms, viruses (including but not limited to human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, and the like), prions, parasites, fungi, mold, yeast and bacteria (both gram-positive and gram-negative) including, among others, *Candida albicans, Aspergillus niger, Escherichia coli (E. coli), Pseudomonas aeruginosa (P. aeruginosa),* and *Staphylococcus aureus (S. aureus),* Group A streptococci, *S. pneumoniae, Mycobacterium tuberculosis, Campylobacter jejuni, Salmonella, Shigella,* and a variety of drug resistant bacteria. Antimicrobial activity can be achieved on various surfaces, such as skin or inorganic surfaces (e.g., countertops, door handles, faucets, telephones beds/bed frames, bed linens, medical equipment, computers, writing instruments, surgical equipment, etc.). The formulation may be in gel, cream, lotion, powder or spray form, and may be embedded within a material or coated onto a material. Surgical garments and gloves may contain (e.g., be treated with) several embodiments of the formulations described herein. Formulations described herein may also be used in transportation, tourist and food industries. Preservation of food and beverages may be accomplished by using several embodiments of the formulations described herein.

Depending on the particular embodiment, certain ingredients listed herein that are generally associated with a particular function may also have other functions, including functions within other general categories listed, as well as other functions that are appreciated in the art.

Adjunct Beneficial Effects

In addition to the benefits of the broad-spectrum efficacy of the formulations disclosed herein and the advantages of the short and long-term effects, formulations disclosed herein provide other beneficial effects as well. For example, in several embodiments, the use of moisturizers or other emollient compounds provide a substantial moisturizing effect to the skin of the user of the formulation. Not only does this improve the general tactile feel of the subject's skin, the increased moisture in the skin provides a more effective natural barrier to prevent microbial infections. For example, properly moisturized skin is less prone to cracking and flaking or other forms of irritation that may foster microbial growth. In conjunction, the formulations disclosed herein are formulated in a manner that reduces the drying effect of the skin. Thus, in certain embodiments, the components of the formulations work synergistically with one another to reduce the ability of microorganisms to populate the skin of an individual into improve the overall health of the skin of an individual. In some embodiments, the formulations are applied to broken or damaged skin (e.g., a laceration, scrape, cut, burn, incision, etc.), and thereby reduce or prevent microbial growth, which concurrently reduces the potential for infection and/or scarring.

In view of these benefits beyond the anti-microbial activity of the formulations, the formulations and several embodiments foster better user compliance than existing antimicrobial formulations. This is because, at least in part, the formulations disclosed herein provide a better tactile feel, less residue, or an improvement in skin health as a result of their use. This increased user compliance subsequently reduces transmission of microorganisms by virtue of the fact that the formulations of are used more regularly. In several embodiments, however, that "regular" use does not necessarily, depending on the embodiment, correspond to increased frequency of use. This is because, at least in part, the persistent effect of the formulations disclosed herein allows a longer duration of time between uses, yet still allows for substantial (or complete) inhibition or kill microorganisms. Advantageously, the persistent effect and the resultant long-term inhibition or kill of microorganisms in some embodiments, reduces the overall cost to a facility for supplying an antimicrobial formulation because the required frequency of use is reduced. In some embodiments, however, more frequent use occurs, such as, for example, in certain situations where microorganism load is anticipated to be greater than normal. Alternatively, in some embodiments, users of the formulation can self-select an appropriate frequency of use, based on their own environments and or desires with respect to the tactile feel of the formulation, and the resultant moisturizing qualities.

In some embodiments, the formulations are prepared without the use of certain art-recognized antimicrobial compounds. For example, in several embodiments, the formulations are triclosan-free. In some embodiments, the formulations are free from silver (or other metal) nanoparticles. In several embodiments, the formulations are free of nonorganic antibiotics and/or organic biocides.

In several embodiments, an additional added benefit of the formulations is the shelf-life stability. The formulations are suitable for storage after production for a period ranging from several months up to several years. For example, in several embodiments the formulations are stable (e.g., retain antimicrobial activity) for about 6 months to about 12 months, about 12 months to about 18 months, about 18 months to about 24 months, or overlapping ranges thereof. Additionally in some embodiments, the formulations are heat stable. This is advantageous, in several embodiments b/c the formulations can be shipped to, stored, and used in rural environments where the temperatures may be higher (e.g., facilities without air conditioning). In several embodiments, the formulations are non-flammable. In several embodiments, the formulations are non-combustible.

Moreover, the formulations are useful in a variety of different dispensers or containers. The formulations, depending on the embodiment, are suitable for dispensing from a wall mount dispenser, a hand pump container, a tube or bottle, an aerosol container, or a tub.

In several embodiments, the above-referenced compounds can be used in various, non-limiting combinations in order to provide a formulation that is optimized for a particular purpose (e.g., targeting preferentially a particular type (or types) of microorganism, killing or inhibiting at a certain level, etc.). Moreover, in several embodiments, the above referenced compounds that make up any given embodiment of the formulation may recognized by those of skill in the art by commercial or trade names, chemical nomenclature of formula, or the International Nomenclature for Cosmetic Ingredients designation.

EXAMPLES

The following studies were designed to test several embodiments of the formulations and methods disclosed herein in terms of their ability to reduce microbial load over time. Various microbes were tested in the experiments, and antimicrobial effects were measured at various time points to assess immediate and persistent antimicrobial effects.

Several examples discussed in more detail below involve antimicrobial testing using Staphylococcus aureus (or MRSA, where specifically indicated) and/or E. coli. These bacteria represent two examples, one gram positive, and one gram negative, respectively, of a variety of microorganisms that are responsible for illness and disease throughout various environments/communities and, given the relative severity of infection with these (or other) microorganisms, reduction in the colonization of surfaces with such microorganisms can, in several embodiments, significantly reduce spread and incidence of infections caused by these bacteria, other drug resistant bacteria, and other varieties of microorganisms.

Example 1—Testing of Persistent and Non-Persistent Soaps

Duration testing was carried out using a modification of the ASTM 1882 method for hand soap. In brief, agar plates were grown to a population of $5 \times 10^3$ S. aureus and then treated with one of several formulations. Microbial counts were taken a 2 minutes, 60 minutes, and 240 minutes. After treatment, the percent reduction and log reduction were calculated for each time point.

TABLE 1

Percentage reduction in S. aureus post-treatment.

| | % Reduction for Each Formulation | | |
| --- | --- | --- | --- |
| Time Point (minutes) | Formulation 1 (contains triclosan) | Formulation 2 (Persistent; triclosan free) | Formulation 3 (Non-persistent; triclosan free) |
| 2 | 100 | 99.67 | 91.64 |
| 60 | 100 | 92.90 | 58.82 |
| 240 | 99.96 | 83.53 | 46.55 |

TABLE 2

$Log_{10}$ reduction in S. aureus post-treatment.

| | % Reduction for Each Formulation | | |
| --- | --- | --- | --- |
| Time Point (minutes) | Formulation 1 (contains triclosan) | Formulation 2 (Persistent; triclosan free) | Formulation 3 (Non-persistent; triclosan free) |
| 2 | 3.50 | 1.49 | 1.09 |
| 60 | 3.69 | 1.16 | 0.40 |
| 240 | 3.50 | 0.79 | 0.27 |

These results demonstrate that each formulation resulted in substantial and/or complete reduction in microbial load, depending on the time point tested and the formulation. Formulations 2 and 3, persistent and non-persistent formulations, respectively, provide an unexpected degree of efficacy against S. aureus given that the formulations are triclosan-free. In several embodiments, other formulations are also triclosan-free, which advantageously allows efficacious antimicrobial effects without the adverse effects associated with triclosan.

In several embodiments, the persistent and non-persistent soap formulations are particularly advantageous due to the rate at which the antimicrobial effects are realized. For example, in several embodiments, the antimicrobial effects (e.g., substantial or complete kill) are achieved after a fraction of the time required for antimicrobial effects to be achieved with other existing formulations. In several embodiments, the time to achieve antimicrobial effects ranges from about 2 to about 5 seconds of hand washing with the formulation, about 5 to about 7 seconds of hand washing, about 7 to about 10 seconds of hand washing, about 10 to about 12 seconds of hand washing, about 12 to about 15 seconds of hand washing, about 15 to about 18 seconds of hand washing, about 18 to about 20 seconds of hand washing, about 20 to about 25 seconds of hand washing, about 25 to about 30 seconds of hand washing, and overlapping ranges thereof. This rapid effect is advantageous because existing formulations require a significantly longer time of constant hand washing, on the order of minutes. Because the vast majority of users of existing formulations fail to perform the hand washing for the requisite period of time, those users are not receiving the full antimicrobial effect that such formulations provide. Thus, the presently described formulations compensate, in several embodiments, for a degree of user error by inducing a more substantial antimicrobial effect despite the lesser degree of time of actual hand washing.

Example 2—Testing of Variant Persistent and Non-Persistent Soap Formulations Duration testing was carried as described above using a modification of the ASTM 1882 method for hand soap.

Variants of certain persistent and non-persistent soap formulations were tested. Percent reduction and log reduction were calculated for each time point.

TABLE 3

Percentage reduction in S. aureus post-treatment.

% Reduction for Each Formulation

| Time Point (minutes) | Formulation 2 | Formulation 2 with 0.7% Farnesol | Formulation 2 with 5% Benzyl Alcohol | Formulation 2 with 2.5% DMSO |
|---|---|---|---|---|
| 2 | 97.6 | 97.6 | 93.8 | 96.6 |
| 60 | 97.8 | 94.9 | 88.4 | 85.7 |
| 240 | 95.4 | 91.4 | 90.9 | 86.7 |

TABLE 4

$Log_{10}$ reduction in S. aureus post-treatment.

Log Reduction for Each Formulation

| Time Point (minutes) | Formulation 2 | Formulation 2 with 0.7% Farnesol | Formulation 2 with 5% Benzyl Alcohol | Formulation 2 with 2.5% DMSO |
|---|---|---|---|---|
| 2 | 1.63 | 1.63 | 1.2 | 1.47 |
| 60 | 1.37 | 1.30 | 0.94 | 0.85 |
| 240 | 1.34 | 1.06 | 1.04 | 0.88 |

These data appear to demonstrate that, certain formulations provide unexpectedly efficacious antimicrobial activity, despite using lesser quantities of certain agents. Addition of either benzyl alcohol or DMSO (which would be expected to increase the antimicrobial effects of the formulations) also failed to increase the antimicrobial effect over that achieved by Formulation 2 alone, in one embodiment. In several embodiments the various components of the formulations disclosed herein have been optimized to provide antimicrobial effects that are unexpected in view of conventional wisdom that suggests that "more is better". In several embodiments, as discussed above other essential oils (e.g., either in addition to or in place of farnesol) can be used and, depending on the embodiment different amounts can be used. In several embodiments, the use of other essential oils, either alone or in combination with farnesol continue to provide potent antimicrobial effects, even when less of that particular component is used, as compared to what conventional wisdom indicates and/or other commercial formulations employ. The formulations disclosed herein comprise, in several embodiments, agents that synergistically work in combination to provide surprisingly efficacious immediate and/or persistent antimicrobial effects.

Example 3—Antimicrobial Testing of Lotion Formulations

Duration of efficacy was carried out using a modification of the ASTM E 1882 method. In brief, the test employed pig skin samples (approximately 16 cm$^2$) as the test application surface for the formulations. The pig skin was exposed to an inoculum of 5×10$^3$ Escherichia coli and then treated with one of a variety of formulations. Bacterial counts were made at 2 minutes, 60 minutes, and 240 minutes.

TABLE 5

Percentage reduction in E. Coli after leave-on treatment

| Formulation | Description | Time Point (minutes) | | |
|---|---|---|---|---|
| | | 2 | 60 | 240 |
| A | Base Lotion (comprises farnesol and benzethonium chloride) | 94 | 91 | 87 |
| B | Base + 0.6% zinc gluconate | 94 | 92 | 88 |
| C | Base + 0.3% zinc gluconate + 0.3% zinc lactate | 94 | 92 | 85 |
| D | Base + 0.1% zinc gluconate + 0.1% zinc lactate | 97 | 96 | 89 |
| E | Base + 1.5% polyaminopropyl biguanide | 98 | 96 | 95 |
| F | Base + 0.1% *Eucalyptus* Oil | 95 | 94 | 91 |
| G | Base + 0.25% Quaternized hydroxyethyl cellulose | 95 | 91 | 87 |
| H | Base + 0.1% Barcleans | 95 | 94 | 81 |
| I | Base + 0.3% zinc gluconate + 0.3% zinc lactate + 0.1% *eucalyptus* oil + 1.5% polyaminopropyl biguanide | 93 | 92 | 81 |
| J | Base + 0.25% Quaternized hydroxyethyl cellulose + 0.3% zinc gluconate + 0.3% zinc lactate + 0.1% Barcleans | 96 | 91 | 86 |
| K | Formulation J + 2.5% DMSO | 97 | 94 | 88 |

TABLE 6

Log reduction in E. Coli after leave-on treatment

| Formulation | Description | Time Point (minutes) | | |
|---|---|---|---|---|
| | | 2 | 60 | 240 |
| A | Base Lotion (comprises farnesol and benzethonium chloride) | 1.22 | 1.08 | 0.91 |
| B | Base + 0.6% zinc gluconate | 1.21 | 1.13 | 0.93 |
| C | Base + 0.3% zinc gluconate + 0.3% zinc lactate | 1.19 | 1.13 | 0.82 |
| D | Base + 0.1% zinc gluconate + 0.1% zinc lactate | 1.54 | 1.38 | 0.97 |
| E | Base + 1.5% polyaminopropyl biguanide | 1.82 | 1.37 | 1.34 |
| F | Base + 0.1% *Eucalyptus* Oil | 1.30 | 1.21 | 1.06 |
| G | Base + 0.25% Quaternized hydroxyethyl cellulose | 1.36 | 1.09 | 0.91 |
| H | Base + 0.1% Barcleans | 1.29 | 1.26 | 0.73 |
| I | Base + 0.3% zinc gluconate + 0.3% zinc lactate + 0.1% *eucalyptus* oil + 1.5% polyaminopropyl biguanide | 1.16 | 1.13 | 0.72 |
| J | Base + 0.25% Quaternized hydroxyethyl cellulose + 0.3% zinc gluconate + 0.3% zinc lactate + 0.1% Barcleans | 1.56 | 1.07 | 0.86 |
| K | Formulation J + 2.5% DMSO | 1.55 | 1.26 | 0.95 |

As shown in the data above, several embodiments of the formulations disclosed herein are effective at reducing microorganism load over an extended period of time. In several embodiments, the persistent effect kills at least about 80% of the microorganisms for a period of time of at least 4 hours. In some embodiments, greater percentages of microorganism death are achieved, for example from about 80% to about 85%, about 85% to about 90%, about 90% to about 91%, about 91% to about 92%, about 92% to about 93%, about 93% to about 94%, about 94% to about 95%, about 95% to about 96%, about 96% to about 97%, about 97% to about 98%, about 98% to about 99%, about 99% to about 100%, and overlapping ranges thereof. In several embodiments, the persistent effect lasts for greater than 4 hours, e.g., about 4 to about 5 hours, about 5 to about 6 hours, about 6 to about 7 hours, about 7 to about 8 hours, about 8 to about 9 hours, about 9 to about 10 hours, or overlapping ranges thereof. In several embodiments, the persistent effect is beneficial in that the number of uses a subject requires is reduced over a given period of time. This not only makes the formulations more cost-effective, but also increases user compliance, as compliance is less (or non-) intrusive into an activity or activities performed by a subject. In some embodiments, however, there are also benefits to more frequent uses (e.g., improved skin quality and feel due to the formulations).

The results presented above illustrate the surprisingly effective nature of certain formulations as broad spectrum antimicrobials having a two-phase antimicrobial effect (e.g., a short-term very high kill phase and a persistent high kill phase). For example, the formulation comprising the base lotion plus 1.5% polyaminopropyl biguanide, with a 98% reduction at 2 minutes and 96% reduction at 60 minutes, still maintains a 95% reduction in E. coli. (1.134 log reduction), even at 240 minutes. The unexpectedly effective dual action immediate and persistent effects are, in several embodiments, a result of the synergistic interactions between the components of the formulation. Similarly, the base lotion supplemented with eucalyptus oil, a non-limiting example of an essential oil, shows not only a high immediate microbial reduction, but a substantially maintained persistent effect as well. In some embodiments, the formulations can comprise only the immediate effects.

The range of applications of the formulations disclosed herein, and the corresponding methods, is wide. For example the formulations can be employed in a variety of environments, including but not limited to hospitals, dental offices, specialty surgical suites, physician offices, care-provided homes, or other medical care facilities, emergency vehicles (e.g., ambulances or fire engines), restaurants, food preparation areas (e.g., butcher shops, grocery stores), public or private transportation vehicles or venues, schools, playgrounds, sports or exercise venues, residential housing (e.g., dormitories, hostels, or hotels), etc.

Example 4—Antimicrobial Testing of Sanitizer Formulations Against E. Coli

Testing was performed as described above, and surfaces were treated with various sanitizer formulations. Bacterial counts were made a 2 minutes, 60 minutes, and 240 minutes.

TABLE 7

Percentage Reduction in E. Coli After Sanitizer Application

| | | Time Point (minutes) | | |
|---|---|---|---|---|
| Formulation | Description | 2 | 60 | 240 |
| L | Commercial Formulation 1 | 96 | 96 | 76 |
| M | Sanitizer Formulation 1 | 98 | 96 | 91 |
| N | Sanitizer Formulation 2 | 95 | 94 | 88 |

TABLE 8

Log Reduction in E. Coli After Sanitizer Application

| | | Time Point (minutes) | | |
|---|---|---|---|---|
| Formulation | Description | 2 | 60 | 240 |
| L | Commercial Formulation 1 | 1.52 | 1.37 | 0.63 |
| M | Sanitizer Formulation 1 | 1.84 | 1.46 | 1.03 |
| N | Sanitizer Formulation 2 | 1.28 | 1.21 | 0.94 |

The results presented above illustrate the surprisingly effective nature of the sanitizer formulations disclosed herein as broad spectrum antimicrobials having a two-phase antimicrobial effect (e.g., a short-term very high kill phase and a persistent high kill phase). As shown above, application of sanitizer formulation 1 results in a 2% improvement in immediate microbial reduction at 2 minutes (98% reduction; 1.84 log), which is maintained at a surprisingly high level, even out to 240 minutes. At that long-term test point, the commercial formulation resulted in only 76% microbial reduction, while sanitizer formulation 1 maintained a 91% reduction (1.03 log). This dual-action effect, based in several embodiments on the synergistic nature of the components of the sanitizer formulation, is particularly advantageous as it is not only reduces microbial load on contact with a surface, but prevents transmission of the microbes over a long period of time. In several embodiments, these effects are also achieved, at least in part, due to the physical characteristics of the formulation. For example, in several embodiments the formulations have a viscosity that allows for improved coverage of a surface (e.g., spreadability) without being overly liquid (which in some cases could lead to undesired flow off of the target surface). In some embodiments, the formulations also have a rapid drying time, which prevents, at least to some degree, the unintended loss of the formulation from a target surface. In several embodiments, low absorption of the formulation into the surface (e.g., skin) also improves the coverage. In yet other embodiments, the formulation is configured to absorb into or adhere to the surface of the skin to achieve persistence.

These results demonstrate that persistence can be achieved with a variety of formulations. However, in several embodiments certain formulations provide unexpectedly greater degrees of antimicrobial activity over time, even with high levels of short-term efficacy. As discussed above, the combination of short and long-term efficacy, as well as the wide spectrum effects (e.g., as demonstrated by the ability to kill the more difficult gram-negative bacteria) yield formulations which are unexpectedly beneficial in view of existing formulations.

Example 5—Sanitizing Formulations Demonstrate Broad Spectrum and Rapid Antimicrobial Effects In recent years, alcohol-based hand sanitizers developed into the dominant products for hand antisepsis in the absence of water. Products having between about 60% and about 95% alcohol are currently the only sanitizers recommended for use in hospitals by the CDC (see, e.g., Centers for Disease Control and Prevention, Hand Hygiene in Healthcare Settings, May 19, 2011, http://www.cdc.gov/handhygiene/). In such settings, the alcohol concentration functions to rapidly kill of a broad spectrum of bacteria, including gram positive and negative bacteria.

However, certain alcohol sanitizers still present significant limitations and drawbacks to their use. Studies have shown that using certain high concentration alcohol sanitizers in hospitals is equivalent to handwashing alone, but does not result in the desired reduction in the occurrence of hospital-acquired infections (HAIs), which can impact about 1 in 20 hospitalized patients and kill nearly 90,000 Americans each year. Certain high concentration alcohol sanitizers can result in a significant drying effect on the hands which can reduce compliance (e.g., reduced and/or ineffective frequency of use). For example, alcohol products can dry the hands with repeated use may result in cracked and painful skin (which could lead to conditions that promote infections). Even trained healthcare workers may only follow recommended hand hygiene protocols a portion the time, which can be, at least in part, due to the drying nature of alcohol-based products. Reduced use/compliance is clinically relevant because alcohol products are effective until such time that they evaporate, typically about 15 seconds. After this time, hands may become immediately re-contaminated, as there is no persistent activity (another limitation of alcohol-based products). Further, the reduced compliance, and increased likelihood of contamination can foster germ transmission from patients and staff, and vice versa.

Another significant limitation of certain alcohol sanitizers is the relatively lower efficacy against many viruses, for example, they largely ineffective against non-enveloped viruses. Non-enveloped viruses are a significant cause of disease in healthcare settings and in homes. Non-limiting of non-enveloped viruses include, but are not limited to, Norovirus (leading cause of acute gastroenteritis or the "stomach flu"), rhinoviruses (common colds), rotavirus (severe diarrhea, especially in children), adenoviruses (tonsillitis and conjunctivitis) and Hepatitis A, among others. The relative lack of efficacy of alcohol against such viruses clinical significance, as a study involving use of an alcohol sanitizer found the alcohol sanitizer to be less effective than rinsing with water alone against Norovirus, only reducing concentration by 0.14-0.34 log. An additional study reported that nursing homes facilities that relied on alcohol products instead of handwashing were more than six times as likely to have a Norovirus outbreak. Further, cruise ships, another closed environment where Norovirus is dangerous, have averaged 16 outbreaks a year, despite the widespread use of alcohol sanitizers. In elementary school settings, where germ transmission can rapidly lead to widespread illness-related absenteeism, studies showed that alcohol-based products, decreased illness-related absenteeism by only 19% in one study and result in no change in a another. However, antiseptic lotion and antiseptic foaming soap formulations according to several embodiments herein were provided to two schools for placement in commonly used areas (e.g., by the door, in the bathrooms). Through collection of over 6,000 data points, these formulation reduced absenteeism by nearly 42% among students (41.6%) and nearly 25% among teachers and staff (24.7%). These results demonstrate that the formulations disclosed herein, in several embodiments, outperform alcohol-based sanitizers and can coordinately reduce absenteeism, lost work/study time, etc. These non-laboratory setting data show that the formulations herein have a real world efficacy, which was further investigated in the laboratory controlled example discussed below.

The present experiments were designed to evaluate the rapid and broad-spectrum efficacy of alcohol-based and non-alcohol-based sanitizing products according to the compositions disclosed herein that seek to address the limitations of certain traditional alcohol-based products.

Methods

The experiments compared an alcohol-based Antiseptic (comprising, according to one embodiment, 70% ethyl alcohol v/v, "EtOH Antiseptic"), a water-based Antiseptic Lotion (comprising a quaternary ammonium, such as, according to one embodiment, benzethonium chloride at 0.2%, "Antiseptic Lotion"), and a Foaming Hand Soap (comprising, according to one embodiment, benzethonium chloride, 0.2%, "Foaming Soap"). This study used an in vitro Time-Kill protocol to evaluate the antiseptic compositions when challenged with 25 different microorganism species as described in the FDA Tentative Final Monograph (see FDA Tentative Final Monograph, Topical Antimicrobial Products for Over-the-Counter Use, 21 CFR 333 and 369, Federal Register 59; 116, 1994). Each product was evaluated at a 99% concentration, and the percent and log reductions were determined following exposure times of 15, 30, and 60 seconds. Agar-plating was performed in duplicate. A combination of clinical isolates and lab strains were used in the testing.

Neutralization studies of each product were also performed versus *Bacteroides fragilis, Escherichia coli, Staphylococcus aureus aureus*, and *Streptococcus pneumoniae* to ensure the neutralizing solution employed (Butterfield's Phosphate Buffer solution with product neutralizers) was effective and non-toxic to each of the representative challenge species.

Results

The log reduction (and percent) due to the EtOH Antiseptic and the Antiseptic Lotion are shown in Table 9.

TABLE 9

Log and Percent Reduction of Various Microorganisms Over Time

| Organism | Time | EtOH Antiseptic | Antiseptic Lotion | Foaming Soap |
| --- | --- | --- | --- | --- |
| *Acinetobacter baumannii* (ATCC #19606) | 15 sec | >6.57 (99.9999%) | >6.57 (99.9999%) | >6.57 (99.9999%) |
|  | 30 sec | >6.57 (99.9999%) | >6.57 (99.9999%) | >6.57 (99.9999%) |
|  | 60 sec | >6.57 (99.9999%) | >6.57 (99.9999%) | >6.57 (99.9999%) |
| *Bacteroides fragilis* (ATCC# 25285) | 15 sec | >7.22 (99.9999%) | 3.87 (99.9864%) | >7.22 (99.9999%) |
|  | 30 sec | >7.22 (99.9999%) | 6.92 (99.9999%) | >7.22 (99.9999%) |
|  | 60 sec | >7.22 (99.9999%) | 3.92 (99.988%) | >7.22 (99.9999%) |
| *Candida albicans* (ATCC# 10231) | 15 sec | >6.16 (99.9999%) | 2.17 (99.3218%) | 0.0460 (10.0346%) |
|  | 30 sec | >6.16 (99.9999%) | 2.75 (99.8208%) | 0.1305 (25.9516%) |
|  | 60 sec | >6.16 (99.9999%) | 3.65 (99.9777%) | 0.5067 (68.8581%) |
| *Candida tropicalis* (ATCC #750) | 15 sec | >6.14 (99.9999%) | 4.14 (99.9927%) | 0.8468 (85.7706%) |
|  | 30 sec | >6.14 (99.9999%) | >6.14 (99.9999%) | 1.3251 (95.2688%) |
|  | 60 sec | >6.14 (99.9999%) | >6.14 (99.9999%) | 2.2873 (99.4839%) |
| *Enterobacter aerogenes* (ATCC #13048) | 15 sec | >6.27 (99.9999%) | >6.27 (99.9999%) | >6.27 (99.9999%) |
|  | 30 sec | >6.27 (99.9999%) | >6.27 (99.9999%) | >6.27 (99.9999%) |
|  | 60 sec | >6.27 (99.9999%) | >6.27 (99.9999%) | >6.27 (99.9999%) |
| *Enterococcus faecalis* (ATCC# 29212) | 15 sec | >6.20 (99.9999%) | 5.38 (99.9996%) | >5.20 (99.9994%) |
|  | 30 sec | >6.20 (99.9999%) | >6.20 (99.9999%) | >5.20 (99.9994%) |

TABLE 9-continued

Log and Percent Reduction of Various Microorganisms Over Time

| Organism | Time | EtOH Antiseptic | Antiseptic Lotion | Foaming Soap |
|---|---|---|---|---|
| | 60 sec | >6.20 (99.9999%) | >6.20 (99.9999%) | >5.20 (99.9994%) |
| Enterococcus faecium (ATCC #6057) | 15 sec | >5.90 (99.9999%) | >5.90 (99.9999%) | 3.4638 (99.9656%) |
| | 30 sec | >5.90 (99.9999%) | >5.90 (99.9999%) | 4.6021 (99.9975%) |
| | 60 sec | >5.90 (99.9999%) | >5.90 (99.9999%) | >4.94 (99.9988%) |
| Escherichia coli (ATCC #11229) | 15 sec | >6.14 (99.9999%) | >6.14 (99.9999%) | 3.2318 (99.9414%) |
| | 30 sec | >6.14 (99.9999%) | >6.14 (99.9999%) | 3.8865 (99.9870%) |
| | 60 sec | >6.14 (99.9999%) | >6.14 (99.9999%) | 4.9389 (99.9988%) |
| Escherichia coli (ATCC #25922) | 15 sec | >5.27 (99.9995%) | >5.27 (99.9995%) | >5.28 (99.9995%) |
| | 30 sec | >5.27 (99.9995%) | >5.27 (99.9995%) | >5.28 (99.9995%) |
| | 60 sec | >5.27 (99.9995%) | >5.27 (99.9995%) | >5.28 (99.9995%) |
| Haemophilus influenzae (ATCC #33930) | 15 sec | >6.23 (99.9999%) | >6.23 (99.9999%) | >5.23 (99.9994%) |
| | 30 sec | >6.23 (99.9999%) | >6.23 (99.9999%) | >5.23 (99.9994%) |
| | 60 sec | >6.23 (99.9999%) | >6.23 (99.9999%) | >5.23 (99.9994%) |
| Klebsiella oxytoca (ATCC #13182) | 15 sec | >6.17 (99.9999%) | >6.17 (99.9999%) | >6.17 (99.9999%) |
| | 30 sec | >6.17 (99.9999%) | >6.17 (99.9999%) | >6.17 (99.9999%) |
| | 60 sec | >6.17 (99.9999%) | >6.17 (99.9999%) | >6.17 (99.9999%) |
| Klebsiella pneumoniae pneumoniae (ATCC #4352) | 15 sec | >6.17 (99.9999%) | >6.17 (99.9999%) | 2.5875 (99.7415%) |
| | 30 sec | >6.17 (99.9999%) | >6.17 (99.9999%) | >6.17 (99.9999%) |
| | 60 sec | >6.17 (99.9999%) | >6.17 (99.9999%) | >6.17 (99.9999%) |
| Micrococcus luteus (ATCC #7468) | 15 sec | >5.40 (99.9996%) | >5.40 (99.9996%) | >4.40 (99.9960%) |
| | 30 sec | >5.40 (99.9996%) | >5.40 (99.9996%) | >4.40 (99.9960%) |
| | 60 sec | >5.40 (99.9996%) | >5.40 (99.9996%) | >4.40 (99.9960%) |
| Proteus mirabilis (ATCC #7002) | 15 sec | >6.08 (99.9999%) | >6.08 (99.9999%) | 3.0634 (99.9136%) |
| | 30 sec | >6.08 (99.9999%) | >6.08 (99.9999%) | 4.5048 (99.9969%) |
| | 60 sec | >6.08 (99.9999%) | >6.08 (99.9999%) | >6.08 (99.9999%) |
| Pseudomonas aeruginosa (ATCC #15442) | 15 sec | >6.29 (99.9999%) | >6.29 (99.9999%) | 4.1264 (99.9925%) |
| | 30 sec | >6.29 (99.9999%) | >6.29 (99.9999%) | 4.5095 (99.9969%) |
| | 60 sec | >6.29 (99.9999%) | >6.29 (99.9999%) | 5.0090 (99.9990%) |
| Pseudomonas aeruginosa (ATCC #27853) | 15 sec | >5.92 (99.9999%) | >5.92 (99.9999%) | 4.9675 (99.9989%) |
| | 30 sec | >5.92 (99.9999%) | >5.92 (99.9999%) | >5.92 (99.9999%) |
| | 60 sec | >5.92 (99.9999%) | >5.92 (99.9999%) | >5.92 (99.9999%) |
| Serratia marcescens (ATCC #14756) | 15 sec | >6.48 (99.9999%) | 5.63 (99.9998%) | 0.0424 (9.3023%) |
| | 30 sec | >6.48 (99.9999%) | >6.48 (99.9999%) | 0.1637 (31.3953%) |
| | 60 sec | >6.48 (99.9999%) | >6.48 (99.9999%) | 0.1564 (30.2326%) |
| Staphylococcus aureus aureus (ATCC #6538) | 15 sec | >6.11 (99.9999%) | 4.09 (99.9919%) | 0.6469 (77.4517%) |
| | 30 sec | >6.11 (99.9999%) | >6.11 (99.9999%) | 1.2928 (94.9035%) |
| | 60 sec | >6.11 (99.9999%) | >6.11 (99.9999%) | 2.8102 (99.8452%) |
| Staphylococcus aureus aureus (ATCC #29212) | 15 sec | >5.56 (99.9997%) | >5.56 (99.9997%) | 0.8706 (86.5278%) |
| | 30 sec | >5.56 (99.9997%) | >5.56 (99.9997%) | 1.1447 (92.8333%) |
| | 60 sec | >5.56 (99.9997%) | >5.56 (99.9997%) | 1.4407 (96.3750%) |
| Staphylococcus epidermidis (ATCC #12228) | 15 sec | >5.45 (99.9996%) | >5.45 (99.9996%) | >4.45 (99.9965%) |
| | 30 sec | >5.45 (99.9996%) | >5.45 (99.9996%) | >4.45 (99.9965%) |
| | 60 sec | >5.45 (99.9996%) | >5.45 (99.9996%) | >4.45 (99.9965%) |
| Staphylococcus haemolyticus (ATCC #29970) | 15 sec | >5.05 (99.9991%) | >5.05 (99.9991%) | >4.05 (99.9910%) |
| | 30 sec | >5.05 (99.9991%) | >5.05 (99.9991%) | >4.05 (99.9910%) |
| | 60 sec | >5.05 (99.9991%) | >5.05 (99.9991%) | >4.05 (99.9910%) |
| Staphylococcus hominis hominis (ATCC #27844) | 15 sec | >4.95 (99.9989%) | >4.95 (99.9989%) | >3.95 (99.9888%) |
| | 30 sec | >4.95 (99.9989%) | >4.95 (99.9989%) | >3.95 (99.9888%) |
| | 60 sec | >4.95 (99.9989%) | >4.95 (99.9989%) | >3.95 (99.9888%) |
| Staphylococcus saprophyticus (ATCC #35552) | 15 sec | >5.88 (99.9999%) | >5.88 (99.9999%) | >4.88 (99.9987%) |
| | 30 sec | >5.88 (99.9999%) | >5.88 (99.9999%) | >4.88 (99.9987%) |
| | 60 sec | >5.88 (99.9999%) | >5.88 (99.9999%) | >4.88 (99.9987%) |
| Streptococcus pneumoniae (ATCC #6303) | 15 sec | >6.29 (99.9999%) | >6.29 (99.9999%) | >5.29 (99.9995%) |
| | 30 sec | >6.29 (99.9999%) | 3.05 (99.9100%) | >5.29 (99.9995%) |
| | 60 sec | >6.29 (99.9999%) | 4.93 (99.9988%) | >5.29 (99.9995%) |
| Streptococcus pyogenes (ATCC #19615) | 15 sec | >6.11 (99.9999%) | >6.11 (99.9999%) | >5.11 (99.9992%) |
| | 30 sec | >6.11 (99.9999%) | >6.11 (99.9999%) | >5.11 (99.9992%) |
| | 60 sec | >6.11 (99.9999%) | >6.11 (99.9999%) | >5.11 (99.9992%) |

The EtOH Antiseptic eliminated at least 99.999% of all organisms tested within 15 seconds. With respect to the duration of time to achieve that amount of microbial reduction, substantially all of the antimicrobial effects occurred in the first 15 seconds, as no differences were detected in kill percentage between the 15 second and 60 second timepoints.

The Antiseptic Lotion was also highly effective against the tested microorganisms, destroying more than 99.99% of 24 of 25 organisms within 15 seconds. The Antiseptic Lotion showed a slightly reduced efficacy against *Candida albicans*, a fungal yeast, showing a 99.32% kill on contact. Against the 23 bacterial strains, the Antiseptic Lotion averaged a 99.999% kill within the first 15 seconds. In the analysis of duration of time to achieve the kill, 99.97% of the antimicrobial effect was achieved within the first 15 seconds of contact of the Antiseptic Lotion with the microorganisms. The results of the duration analysis are show in Table 10.

TABLE 10

Duration of Time to Achieve Maximum Antimicrobial Effects

| | EtOH Antiseptic | Antiseptic Lotion | Difference |
|---|---|---|---|
| Average Kill at 15 seconds | 99.9998% | 99.9715% | 0.028% |
| Average Kill at 30 seconds | 99.9998% | 99.8990% | 0.011% |
| Average Kill at 60 seconds | 99.9998% | 99.9988% | 0.001% |
| Percent of total effect achieved in first 15 seconds | 100% | 99.97% | 0.03% |

The Foaming Soap had a less rapid effect against certain microorganisms, buy still exhibited substantial anti-microbial effects against nearly all the microorganisms tested. The longer time to efficacy, in several embodiments, is due to the formulation of the soap and the intended use of certain embodiments of the formulation (e.g., hand washing for recommended times and with recommended temperature water). Despite having lesser antimicrobial effects on an acute (e.g., 15-30 seconds) as compared to the EtOH Antiseptic and the Antiseptic Lotion, the Foaming Soap still exhibited microbial reduction of 99% or greater at 60 seconds against 22 of the 25 microorganisms tested. The rate of antimicrobial effects is particularly surprising and unexpected, as the antiseptic lotion, in several embodiments, is alcohol-free. Thus, in several embodiments, the antiseptic lotion provides rapid effects (and longer term effects which are discussed more below) without the potential adverse effects associated with certain alcohol based products. Thus, in several embodiments, the Foaming Soap is particularly advantageous as an antimicrobial agent, particularly when handwashing conditions of 60 seconds or more are employed. In several embodiments, color changing agents or other indicators are provided to indicate optimal efficacy (e.g., the soap changes color or consistency after 60 seconds).

The experiments in this Example employ a standard protocol, and as such, the results can be compared against products that contain various concentrations of ethanol (or other alcohol) alone, to compare the immediate kill of the antiseptic products disclosed herein against a standard alcohol product. As shown in Table 11, a commercially available alcohol-based sanitizer (61% alcohol) was tested against an alcohol-based antiseptic according to several embodiments disclosed herein, and an antiseptic lotion according to several embodiments disclosed herein.

TABLE 11

Comparison of Antimicrobial Activity Against Commercially Available Alcohol-Based Sanitizer

| | AVAGARD D Sanitizer | EtOH Antiseptic | Antiseptic Lotion |
|---|---|---|---|
| S. aureus | 99.1% | 99.9997% | 99.9997% |
| S. epidermis | >99.9% | 99.9996% | 99.9996% |
| K. pneumoniae | >99.9% | 99.9999% | 99.9999% |
| P. aeruginosa | >99.9% | 99.9999% | 99.9999% |
| E. coli | >99.9% | 99.9999% | 99.9999% |
| S. pneumoniae | >99.9% | 99.9999% | 99.9999% |
| S. pyogenes | 98.0% | 99.9999% | 99.9999% |
| S. marcescens | >99.9% | 99.9999% | 99.9998% |
| E. faecalis | >99.9% | 99.9999% | 99.9996% |

These results demonstrate that both the EtOH Antiseptic according to several embodiments disclosed herein and the Antiseptic Lotion according to several embodiments disclosed herein achieved not only a rapid kill effect but also a broad-spectrum kill against a wide variety of microorganisms. The antimicrobial effect of the EtOH Antiseptic and the Antiseptic Lotion according to several embodiments disclosed herein was greater than that achieved by a commercially available Sanitizer (AVAGUARD D), reducing bacterial load by over ~2 log against the microorganisms tested (notably, these include both E. coli and S. aureus).

Surprisingly, the immediate, broad-spectrum kill profile is substantially similar between the EtOH Antiseptic and the Antiseptic Lotion (which is water-based). Results of this time-kill testing eliminate the concern that a non-alcohol product cannot have the same rapid antimicrobial benefits as an alcohol-based sanitizer. Furthermore, this time-kill study demonstrated that both the Antiseptic and Antiseptic Lotion had a greater immediate kill than a traditional, alcohol-only sanitizer. In several embodiments, the EtOH sanitizer, despite its relatively high alcohol concentration, is not associated with several of the adverse effects of traditional alcohol-based sanitizers, due to, for example, additional ingredients that provide moisturizing and/or protective effects on the skin. Moreover these results indicate that the Antiseptic Lotion (which is water based) is at least equivalent to certain alcohol-based products currently used in healthcare facilities for immediate, broad-spectrum kill. These superior results are particularly surprising given that the Antiseptic Lotion is water-based, given that alcohol is responsible for a substantial amount of antimicrobial effects in many alcohol-based products. In several embodiments, the use of a water-based product may reduce skin irritation, improve compliance, eliminate concerns about flammability and storage, and add a persistent effect to the products, each of which contributes to the increased efficacy of the Antiseptic Lotion. In several embodiments, the formulations are non-flammable. In several embodiments, the formulations are non-combustible.

Example 6—Efficacy of Sanitizing Formulations in In Vivo Healthcare Personnel Wash Testing As discussed above, Hospital Acquired Infections (HAI) are a major source of morbidity and mortality. Health-care associated pathogens transmitted not only from infected or draining wounds, but also from frequently colonized areas of normal, intact patient skin. For example, patients with diabetes, patients undergoing dialysis for chronic renal failure, and those with chronic dermatitis are likely to have areas of intact skin that are colonized with S. aureus. While data suggests that direct patient contact and respiratory-tract care are most likely to contaminate the fingers of caregivers and duration of patient-care activity was strongly associated with the intensity of bacterial contamination of health care provider hand, patient gowns, bed linen, bedside furniture, and other objects in the patient's immediate environment can easily become contaminated with patient flora. Transmission from patient to health care workers can then result in re-transmission to another patient, another health care worker, or to individuals outside the health care setting. In any event, the transmission and re-transmission of microorganisms can result in wide-spread infections and associated illnesses.

Efforts to reduce the infection of health care workers and spread of microorganisms (and incidence if HAIs) are commonly manifest in handwash procedures. The present experiment was designed to evaluate the efficacy of certain sanitizing formulations disclosed herein when used according to 21 CFR parts 333 and 369, Topical Antimicrobial Drug Products for Over-the-Counter Human Use; Tentative Final Monograph (TFM) for Health-Care Antiseptic Drug Products; Proposed Rule.

Methods

A total of fifty-two subjects were subjected to eleven consecutive hand contaminations with *Serratia marcescens* (ATCC #14756). Subjects were assigned randomly to use of one of the two test products or the reference product (e.g., each subject was assigned to use one, and only one, of the three test materials). After the first contamination, a baseline sample was obtained, and thereafter, the remaining 10 contaminations were performed, each following by application of one of the test products. Microbial samples were taken after product applications 1, 3, 7, and 10. Data from a total of forty-six subjects were included in the statistical analysis with data from 16 subjects included for Test Product #1, data from 15 subjects included for Test Product #2, and data from 15 subjects included for the Reference Product. Mean $\log_{10}$ reductions of *S. marcescens* were used to evaluate the antimicrobial efficacy of each test product. The two test products were the EtOH Antiseptic and the Antiseptic Lotion (from Example 5). The commercially available reference product was HIBICLENS®, which comprises a 4% (w/v) solution of chlorhexidine gluconate.

A stock culture of *S. marcescens* was prepared by aseptically transferring a lyophilized pellet to approximately 5.0 mL of sterile Tryptic Soy Broth (TSB), which was then incubated at 25° C.±2° C. for 24 hours±4 hours. A 2-L flask containing approximately 1,000 mL TSB was inoculated with 1.0 mL of the 24-hour broth culture, and incubated for 24 hours±4 hours at 25° C.±2° C. Prior to any withdrawal of culture, whether for hand contamination or for numbers assay, the suspension was stirred or swirled. The suspension was assayed for number of organisms at the beginning and end of the use period. A suspension was not used in testing for more than 8 hours.

Each subject was in testing for 3.5 to 4.5 hours on a single day. Subjects' fingernails clipped were to a free edge of ~1 mm. All jewelry was removed from the hands and arms prior to the inception of the study period. Using tap water, a practice hand-inoculation procedure was performed by each subject, to reduce subject-to-subject variation do to application procedures. A 5.0-mL aliquot of a suspension containing approximately $1.0 \times 10^9$ CFU/mL of *S. marcescens* was transferred into each subject's cupped hands in three successive volumes of approximately 1.5 mL, 1.5 mL, and 2 mL, respectively. The inoculum then was distributed evenly over both hands, not reaching above the wrists, via continuous massage for 45 seconds.

After a timed 2-minute air-dry, the Glove Juice Sampling Procedure was performed. That procedure involved the placement of powder-free, sterile latex gloves were on the subjects' hands and instillation of 75.0 mL Stripping Suspending Fluid (SSF) into each of the gloves. The wrists were secured, and attendants massaged the hands through the gloves in a standardized manner for 60 seconds. Thereafter, a sample from each glove was taken to establish baseline recovery values. Additionally, a 5.0-mL aliquot of the glove juice was removed from each of the gloves and separately diluted in 5.0 mL Butterfield's Phosphate Buffer Solution with product neutralizers (BBP++) (dilution $10^0$). The $10^0$ dilutions then were serially diluted in BBP++, as appropriate. Following the Glove Juice Sampling Procedure was a 30-second handwash using nonmedicated soap and a 30-second rinse.

Subsequent contaminations were performed by distributing an additional 5.0 mL of the *S. marcescens* suspension over both hands, not reaching above the wrists, via gentle continuous massage for 45 seconds. A timed 2-minute air-dry was performed, followed by the application of randomly assigned test material to each subject according to the following.

For the EtOH Antiseptic, an amount sufficient to thoroughly wet the subjects' hands, approximately 2 mL to 3 mL, was dispensed into subjects' cupped dry hands. Subjects rubbed the test product over the entire surface of the hands and fingers paying special attention to nails and nail beds, and continued to rub into the skin until dry. Prior to any sample, subjects waited an additional 5 minutes after product appeared dry.

For the Antiseptic Lotion, an amount sufficient to thoroughly wet the subjects' hands, approximately 1 mL to 2 mL, was dispensed into subjects' cupped dry hands. Subjects rubbed the test product over the entire surface of the hands and fingers paying special attention to nails and nail beds, and continued to rub into the skin until dry. Prior to any sample, subjects waited an additional 5 minutes after product appeared dry.

For the Reference Product, subjects wet their hands and forearms and 5 mL of the Reference Product was dispensed into the subjects' cupped hands. Subjects then rubbed their hands together and lathered the product onto their hands and forearms for 30 seconds, followed by a rinse of their hands for 30 seconds. For washes that were followed by a sample, the hands were gloved wet. Subjects lightly dried hands with a disposable paper towel after washes not followed by a sample.

Each subject completed the above contamination/product application a total of 10 consecutive times, with a minimum of 5 minutes between microbe/product applications. Following contamination/product application cycle 9 the subjects assigned to use one of the two test products rinsed their hands for 30 seconds. The hands were sampled for residual *S. marcescens* after contamination/product application cycles 1, 3, 7, and 10. All samples were performed using the Glove Juice Sampling Procedure (discussed above).

Samples were plated on duplicate spiral plates prepared from appropriate dilutions using Tryptic Soy Agar with product neutralizers (TSA+). The plates were incubated at 25° C.±2° C. for approximately 48 hours, or until sufficient growth was observed. *S. marcescens* produces red colonies, and only those colonies were counted. Colonies were counted and data recorded using the computerized Q-COUNT™ plate-counting system. If $10^0$ spiral plates gave an average count of zero, the average plate count was expressed as $1.00 \times 10^1$. A neutralization study (data not shown) assured that the neutralizers used in the recovery medium effectively quenched the antimicrobial activity of the test materials and were not toxic to the challenge species. Study procedures were based on ASTM E 1054-08, Standard Test Methods for Evaluation of Inactivators of Antimicrobial Agents.

The estimated $\text{Log}_{10}$ number of viable microorganisms recovered from each subject's hand was designated the "R-value," the adjusted average $\log_{10}$ colony count measurement from each sample. Each R-value was determined using the following formula: $R = \log_{10} [75 \times C_i \times 10^{-D} \times 2]$, where 75 is the amount (mL) of stripping solution instilled into each glove, $C_i$ is the arithmetic average colony count of the two plate counts from each sample at a particular dilution level, D is the dilution factor, and 2 is the neutralization dilution.

$Log_{10}$ reductions from baseline populations recovered from each of a subject's hands were calculated by subtracting the $log_{10}$ number of viable microorganisms recovered from the hands following product application from the $log_{10}$ number of viable microorganisms recovered for baseline. Mean and standard deviation data were generated on the $log_{10}$ data from baseline samples, post-product application samples, and the reductions from baseline. These data are shown in Tables 12-16.

TABLE 12

Statistical Data of the Mean $Log_{10}$ Microbial Recoveries of *S. marcescens* and Mean $Log_{10}$ Microbial Reductions from Baseline Following Subjects' Use of EtOH Antiseptic

| Sample | Sample Size | Mean | Minimum Value | Maximum Value |
|---|---|---|---|---|
| Baseline $Log_{10}$ Microbial Recovery | 32 | 9.14 | 7.86 | 9.47 |
| Post-Product Application 1 $Log_{10}$ Microbial Recovery | 32 | 6.32 | 5.42 | 7.15 |
| Post-Product Application 3 $Log_{10}$ Microbial Recovery | 32 | 6.72 | 4.89 | 8.23 |
| Post-Product Application 7 $Log_{10}$ Microbial Recovery | 32 | 5.53 | 3.18 | 7.32 |
| Post-Product Application 10 $Log_{10}$ Microbial Recovery | 32 | 5.43 | 3.18 | 6.42 |
| Post-Product Application 1 $Log_{10}$ Reduction from Baseline | 32 | 2.82 | 2.13 | 3.42 |
| Post-Product Application 3 $Log_{10}$ Reduction from Baseline | 32 | 2.42 | 0.97 | 3.95 |
| Post-Product Application 7 $Log_{10}$ Reduction from Baseline | 32 | 3.62 | 1.75 | 5.83 |
| Post-Product Application 10 $Log_{10}$ Reduction from Baseline | 32 | 3.72 | 2.64 | 5.59 |

TABLE 13

Statistical Data of the Mean $Log_{10}$ Microbial Recoveries of *S. marcescens* and Mean $Log_{10}$ Microbial Reductions from Baseline Following Subjects' Use of Antiseptic Lotion

| Sample | Sample Size | Mean | Minimum Value | Maximum Value |
|---|---|---|---|---|
| Baseline $Log_{10}$ Microbial Recovery | 30 | 9.26 | 8.96 | 9.44 |
| Post-Product Application 1 $Log_{10}$ Microbial Recovery | 30 | 7.62 | 6.79 | 8.43 |
| Post-Product Application 3 $Log_{10}$ Microbial Recovery | 30 | 7.64 | 5.94 | 8.64 |
| Post-Product Application 7 $Log_{10}$ Microbial Recovery | 30 | 6.54 | 4.33 | 8.29 |
| Post-Product Application 10 $Log_{10}$ Microbial Recovery | 30 | 6.15 | 4.09 | 8.17 |
| Post-Product Application 1 $Log_{10}$ Reduction from Baseline | 30 | 1.64 | 0.86 | 2.50 |
| Post-Product Application 3 $Log_{10}$ Reduction from Baseline | 30 | 1.63 | 0.66 | 3.37 |
| Post-Product Application 7 $Log_{10}$ Reduction from Baseline | 30 | 2.73 | 0.99 | 4.95 |
| Post-Product Application 10 $Log_{10}$ Reduction from Baseline | 30 | 3.11 | 1.12 | 5.10 |

TABLE 14

Statistical Data of the Mean $Log_{10}$ Microbial Recoveries of *S. marcescens* and Mean $Log_{10}$ Microbial Reductions from Baseline Following Subjects' Use of HIBICLENS ®

| Sample | Sample Size | Mean | Minimum Value | Maximum Value |
|---|---|---|---|---|
| Baseline $Log_{10}$ Microbial Recovery | 30 | 9.14 | 8.35 | 9.42 |
| Post-Product Application 1 $Log_{10}$ Microbial Recovery | 30 | 6.28 | 5.42 | 7.01 |
| Post-Product Application 3 $Log_{10}$ Microbial Recovery | 30 | 5.53 | 4.68 | 6.20 |
| Post-Product Application 7 $Log_{10}$ Microbial Recovery | 30 | 4.91 | 3.96 | 5.67 |
| Post-Product Application 10 $Log_{10}$ Microbial Recovery | 30 | 4.72 | 3.66 | 5.57 |
| Post-Product Application 1 $Log_{10}$ Reduction from Baseline | 30 | 2.85 | 1.59 | 3.76 |
| Post-Product Application 3 $Log_{10}$ Reduction from Baseline | 30 | 3.61 | 2.32 | 4.34 |
| Post-Product Application 7 $Log_{10}$ Reduction from Baseline | 30 | 4.23 | 2.78 | 5.06 |
| Post-Product Application 10 $Log_{10}$ Reduction from Baseline | 30 | 4.42 | 2.78 | 5.42 |

To ensure that the reductions detected were due to product application and not to falling microbial population numbers, the populations of the *S. marcescens* inoculum suspensions used in testing were over the testing period and are presented in Table 15.

TABLE 15

Initial and Final Populations of the *S. marcescens* Inoculum Suspension

| Test Date | Group | Initial Population (CFU/mL) | Final Population (CFU/mL) |
|---|---|---|---|
| Apr. 4, 2013 | 1 (PM) | $1.42 \times 10^9$ | $1.69 \times 10^9$ |
| Apr. 5, 2013 | 2 (PM) | $1.78 \times 10^9$ | $1.65 \times 10^9$ |
| Apr. 12, 2013 | 3 (AM) | $1.62 \times 10^9$ | $1.62 \times 10^9$ |
| Apr. 12, 2013 | 4 (PM) | $1.87 \times 10^9$ | $1.69 \times 10^9$ |
| Apr. 16, 2013 | 5 (AM) | $1.57 \times 10^9$ | $1.62 \times 10^9$ |
| Apr. 16, 2013 | 6 (AM) | $1.59 \times 10^9$ | $1.77 \times 10^9$ |
| Apr. 16, 2013 | 7 (PM) | $1.69 \times 10^9$ | $1.50 \times 10^9$ |

Summary statistics were also generated on the $log_{10}$ reductions from baseline for the EtOH Antiseptic, the Antiseptic Lotion, and for HIBICLENS® (Mölnlycke Health Care, AB), following product applications 1 and 10, and are presented in Table 16.

TABLE 16

Statistical Summary Log$_{10}$ Microbial Reductions from Baseline

|  | N | Mean | Min | Max | Std. Dev. | 95% Std. Dev. Conf. Int. |
|---|---|---|---|---|---|---|
| EtOH Antiseptic Post-Application 1 | 32 | 2.8213 | 2.1313 | 3.4204 | 0.3409 | 0.254295-0.50429 |
| EtOH Antiseptic Post-Application 10 | 32 | 3.715 | 2.641 | 5.591 | 0.685 | 0.511085-1.10354 |
| Antiseptic Lotion Post-Application 1 | 30 | 1.6417 | 0.8550 | 2.4967 | 0.4352 | 0.321774-0.65379 |
| Antiseptic Lotion Post-Application 10 | 30 | 3.107 | 1.117 | 5.099 | 0.931 | 0.688543-1.39899 |
| HIBICLENS ® Post-Application 1 | 30 | 2.8527 | 1.5889 | 3.7591 | 0.4983 | 0.368502-0.74873 |
| HIBICLENS ® Post-Application 10 | 30 | 4.419 | 2.775 | 5.420 | 0.574 | 0.424471-0.86245 |

Figure 2:
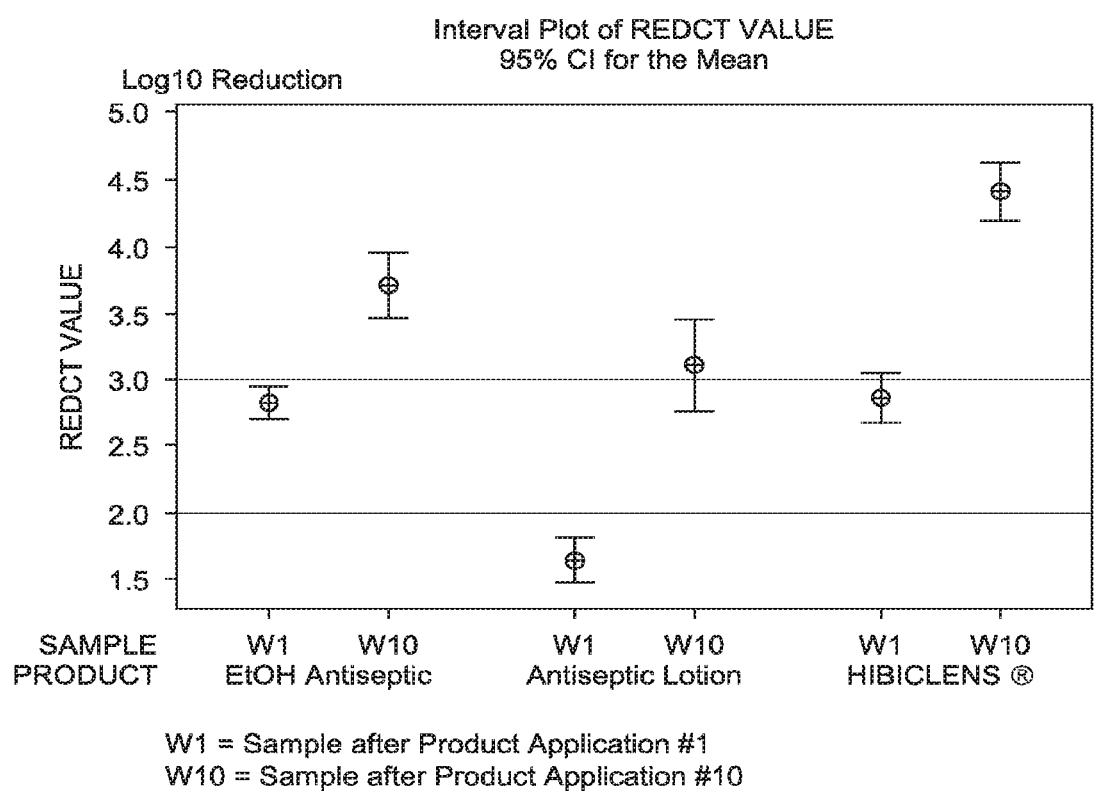
FIG. 2 depicts summary data related to antimicrobial effectiveness of various sanitizing formulations after multiple re-infections with *S. marcescens* and multiple applications of the formulations.

A two-way analysis of variance (ANOVA) was performed to compare the efficacy of the EtOH Antiseptic, the Antiseptic Lotion, and HIBICLENS®. The ANOVA results (calculations not shown) are depicted graphically in FIGS. 1 and 2. These data show that HIBICLENS® and the EtOH Antiseptic showed the same log reduction (from baseline) at application #1. The EtOH Antiseptic showed a 3.5 log reduction, even after 10 re-inoculations with S. marcescens. While the Antiseptic Lotion showed lower reduction at Application 1 as compared to the other products tested, after 10 re-inoculations with S. marcescens, the Antiseptic Lotion showed greater than a 3.0 log reduction in microorganism load.

Figure 3:
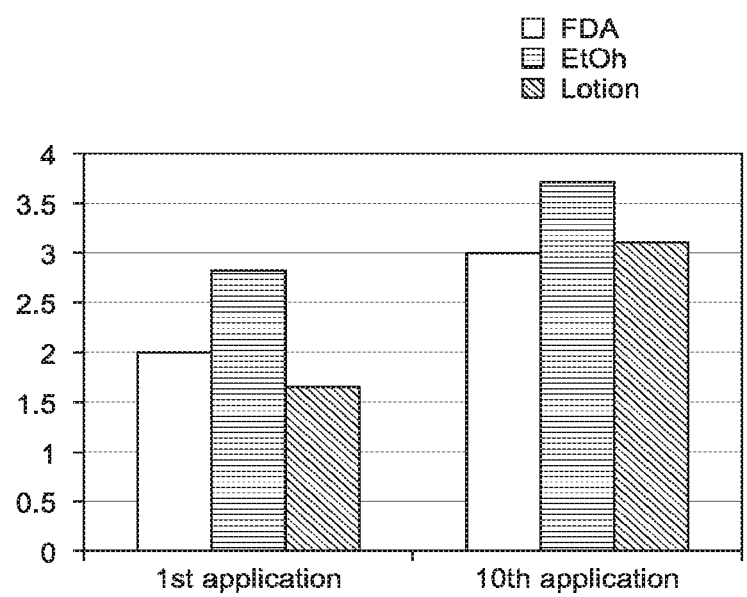
FIG. 3 depicts data related to the antimicrobial effectiveness of various sanitizing formulations disclosed herein against *S. marcescens* as compared to FDA recommended levels of efficacy after multiple applications.

These data demonstrate that, the EtOH antiseptic passed the 2.0 log$_{10}$ reduction at Application 1 and the 3.0 log$_{10}$ reduction at Application 10, per the FDA Healthcare Personnel Handwash Requirements. While the Antiseptic Lotion, at least according to this specific example, did not pass the 2.0 log$_{10}$ reduction at Application 1, it passed the 3.0 log$_{10}$ reduction at Application 10 (see FIG. 3). Of note is that the protocol performed in this example was designed specifically for wash-off hand products (e.g., soaps intended to be rinsed from the hands after use). This protocol employs a significant initial load of microorganism, in the view that the rinsing of the hands after application will result in some (potentially substantial) loss of microorganism. Thus, the higher initial load is to ensure that meaningful microorganism data can be obtained (e.g., lower initial load with hand washing could lead to minimal microorganism counts at a first time point, providing potentially misleading results into the efficacy of a formulation). In the example discussed above, the antiseptic lotion was not washed off (in accordance with the intended use of one embodiment of the formulation), though the FDA protocol initial microorganism load was employed. As such, the reduction in the microorganism count is solely attributable to the application of the antiseptic formulation (and not based on any wash off of the product or microorganism). Thus, the efficacy of the Antiseptic Lotion, while not meeting the initial Application 1 FDA threshold numerically, is significant, in that the threshold was nearly reached, without the "benefit" of a rinse removing microorganisms (which the FDA threshold has accounted for). Based on these results both of these antiseptic formulations, even as compared to a currently available product, produce significant (statistically and clinically) reductions in microorganisms load, even after repeated exposure, as would be expected in a certain settings, such as for example, hospitals, nursing homes, etc.

Example 7—Bacteria-Eliminating Efficacy of Sanitizing Formulations on Adult Hands The present example was conducted to determine the antimicrobial effectiveness of two test products (EtOH Antiseptic and Antiseptic Lotion) using a modification of the standardized test method ASTM E2755-10, Determining the Bacteria Eliminating Effectiveness of Hand Sanitizer Formulations Using Hands of Adults.

A total of six subjects were tested, 3 per test material, over the course of 2 consecutive hand contaminations, the first followed by a sample for baseline, and the second by a product application. As with the Example 6, the indicator microorganism was S. marcescens (ATCC #14756). Mean log$_{10}$ reductions of S. marcescens was the basis for assessing the antimicrobial effectiveness of each test product.

A stock culture of Serratia marcescens (ATCC #14756) was prepared by aseptically transferring a lyophilized pellet to approximately 5.0 mL of sterile TSB, which will then be incubated at 35° C.±2° C. for 25 hours±1 hour. Two 500-mL flasks, each containing approximately 125 mL of TSB, were inoculated with 1.0 mL of the 24-hour broth culture, placed on a platform shaker set at approximately 250 rpm, and incubated for 25 hours±1 hour at 35° C.±2° C. 10.0-mL aliquots from each flask were dispensed into sterile graduated centrifuge tubes and centrifuged at 4750 rpm±50 rpm for 30 minutes or until sedimentation was complete. The supernatant was decanted, and the pellet brought back to a volume of 1.0 mL using TSB. The tubes were vortexed thoroughly and pooled into one container prior to use. Prior to any withdrawal of culture, whether for hand contamination or for numbers assay, the suspension was stirred and/or swirled. The suspension was assayed for number of organisms at the beginning and end of the use period. A suspension was not used for more than 8 hours.

Subjects were assigned randomly to use of one of the two test products (e.g., each person was assigned to use one, and only one, of the two test products). Subjects' fingernails clipped were to a free edge of ~1 mm. All jewelry was removed from the hands and arms prior to the inception of the study period. Using tap water, a practice hand-inoculation procedure was performed by each subject, to reduce subject-to-subject variation do to application procedures. A 0.2-mL aliquot of tap water was transferred into a subject's cupped hands. The tap water was then distributed evenly over both hands, not reaching above the wrists, via gentle continuous massage.

A 30-second handwash using nonmedicated soap and a 30-second rinse was performed to remove dirt and oil from the hands prior to inception of the inoculation experiment. The temperature of the water used for this and subsequent wash procedures was controlled at 40° C.±2° C.

Thereafter, a 0.2-mL aliquot of the inoculum suspension containing approximately $1\times10^{10}$ CFU/mL S. marcescens was transferred into the subject's cupped hands. The inoculum was distributed evenly over both hands, not reaching above the wrists, via continuous massage for 30 seconds±5 seconds. After the timed 30-second massage, the Glove Juice Sampling Procedure was performed.

Within 5 minutes after contamination for baseline and after the single product application, powder-free, sterile latex gloves were placed on subjects' hands, and 75.0 mL Stripping Suspending Fluid (SSF) was instilled into each of the gloves. The wrists were secured, and attendants massaged the hands through the gloves in a standardized manner for 60 seconds. Following sampling a 5.0-mL aliquot of the glove juice was removed from each of the gloves and separately diluted in 5.0 mL Butterfield's Phosphate Buffer Solution with product neutralizers (BBP++) (dilution $10^0$). The $10^0$ dilutions then were serially diluted in BBP++, as appropriate. This first contamination cycle provided the baseline population level. It was followed by a 30-second handwash using nonmedicated soap and a 30-second rinse. Upon completion of the nonmedicated soap wash, subjects were required to wait a minimum of 5 minutes prior to the start of the next contamination/product application cycle.

For the subsequent contamination, a 0.2-mL aliquot of the inoculum suspension was again evenly distributed over both hands, as discussed above. Thereafter, 0.4 mL of either the EtOH Antiseptic or the Antiseptic Lotion was dispensed into subjects' cupped, dry hands (notably, this is a significantly smaller application volume as compared to other commercial formulations). The subjects rubbed the test product over the entire surface of the hands and fingers paying special attention to nails and nail beds, and continued to rub into the skin until dry (as discussed above). Prior to any sample, subjects waited an additional 5 minutes after the relevant product appeared dry on the skin. Thereafter, samples to evaluate the microbial reduction were obtained using the Glove Juice Sampling Procedure (discussed above).

Samples were plated on duplicate spiral plates prepared from appropriate dilutions using Tryptic Soy Agar with product neutralizers (TSA+). The plates were incubated at 25° C.±2° C. for approximately 48 hours, or until sufficient growth was observed. S. marcescens produces red colonies, and only those colonies were counted. Colonies were counted and data recorded using the computerized Q-COUNT plate-counting system. If $10^0$ spiral plates gave an average count of zero, the average plate count was expressed as $1.00\times10^1$. A neutralization study (data not shown) assured that the neutralizers used in the recovery medium effectively quenched the antimicrobial activity of the test materials and were not toxic to the challenge species. Study procedures were based on a modification of ASTM E2755-10, Determining the Bacteria-Eliminating Effectiveness of Hand Sanitizer Formulations Using Hands of Adults. R-values (estimated $Log_{10}$ number of viable microorganisms recovered from each subject's hand) was calculated as discussed in Example 6).

$Log_{10}$ reductions from baseline populations recovered from each of a subject's hands were calculated by subtracting the $log_{10}$ number of viable microorganisms recovered from the hands following product application from the $log_{10}$ number of viable microorganisms recovered for baseline. Statistical calculations of mean and standard deviation were generated on the $log_{10}$ data from baseline samples, post-product application samples, and the reductions from baseline. The statistical results are presented in Tables 17-22.

TABLE 17

Statistical Data of the Mean $Log_{10}$ Microbial Recoveries of S. marcescens and Mean $Log_{10}$ Microbial Reductions from Baseline Following Subjects' Use of 0.4 mL of EtOH Antiseptic

| Sample | Sample Size | Mean | Minimum Value | Maximum Value |
|---|---|---|---|---|
| Baseline $Log_{10}$ Microbial Recovery | 6 | 8.45 | 7.55 | 8.98 |
| Post-product $Log_{10}$ Microbial Recovery | 6 | 6.30 | 5.16 | 7.72 |
| Post-Product Application $Log_{10}$ Reduction from Baseline | 6 | 2.15 | 1.26 | 2.57 |

TABLE 18

$Log_{10}$ Microbial Recoveries of S. marcescens By Subject and Hand Following Subjects' Use of 0.4 mL of EtOH Antiseptic

| Subject | Hand | Baseline $Log_{10}$ Microbial Recovery | Post-product $Log_{10}$ Microbial Recovery | Post-Product Application $Log_{10}$ Reduction from Baseline |
|---|---|---|---|---|
| 8 | Left | 8.98 | 7.72 | 1.26 |
|  | Right | 8.79 | 6.49 | 2.30 |
| 5 | Left | 7.82 | 5.25 | 2.57 |
|  | Right | 7.55 | 5.16 | 2.39 |
| 12 | Left | 8.78 | 6.45 | 2.33 |
|  | Right | 8.80 | 6.75 | 2.05 |

TABLE 19

Statistical Data of the Mean $Log_{10}$ Microbial Recoveries of S. marcescens and Mean $Log_{10}$ Microbial Reductions from Baseline Following Subjects' Use of 0.4 mL of Antiseptic Lotion

| Sample | Sample Size | Mean | Minimum Value | Maximum Value |
|---|---|---|---|---|
| Baseline $Log_{10}$ Microbial Recovery | 6 | 8.33 | 7.90 | 8.64 |
| Post-product $Log_{10}$ Microbial Recovery | 6 | 6.86 | 6.39 | 7.61 |
| Post-Product Application $Log_{10}$ Reduction from Baseline | 6 | 1.47 | 1.03 | 1.83 |

TABLE 20

$Log_{10}$ Microbial Recoveries of S. marcescens By Subject and Hand Following Subjects' Use of 0.4 mL of Antiseptic Lotion

| Subject | Hand | Baseline $Log_{10}$ Microbial Recovery | Post-product $Log_{10}$ Microbial Recovery | Post-Product Application $Log_{10}$ Reduction from Baseline |
|---|---|---|---|---|
| 8 | Left | 7.90 | 6.39 | 1.51 |
|  | Right | 8.42 | 6.60 | 1.83 |
| 5 | Left | 8.58 | 7.29 | 1.29 |
|  | Right | 8.64 | 7.61 | 1.03 |
| 12 | Left | 8.29 | 6.62 | 1.67 |
|  | Right | 8.14 | 6.64 | 1.50 |

To ensure that the reductions detected were due to product application and not to falling microbial population numbers, the populations of the *S. marcescens* inoculum suspensions used in testing were over the testing period and are presented in Table 21.

TABLE 21

Initial and Final Populations of the *S. marcescens* Inoculum Suspension

| Test Date | Group | Initial Population (CFU/mL) | Final Population (CFU/mL) |
|---|---|---|---|
| Apr. 9, 2013 | 1 (PM) | $9.31 \times 10^9$ | $1.09 \times 10^9$ |

Summary statistics were also generated on the $\log_{10}$ reductions from baseline for the EtOH Antiseptic, the Antiseptic Lotion and are presented in Table 22.

TABLE 22

Statistical Summary $\log_{10}$ Microbial Reductions from Baseline

| | N | Mean | Min | Max | Std. Dev. | 95% Std. Dev. Conf. Int. |
|---|---|---|---|---|---|---|
| EtOH Antiseptic | 6 | 2.150 | 1.262 | 2.568 | 0.466 | 0.273134-1.33272 |
| Antiseptic Lotion | 6 | 1.471 | 1.028 | 1.826 | 0.282 | 0.165332-0.80672 |

Figure 4:
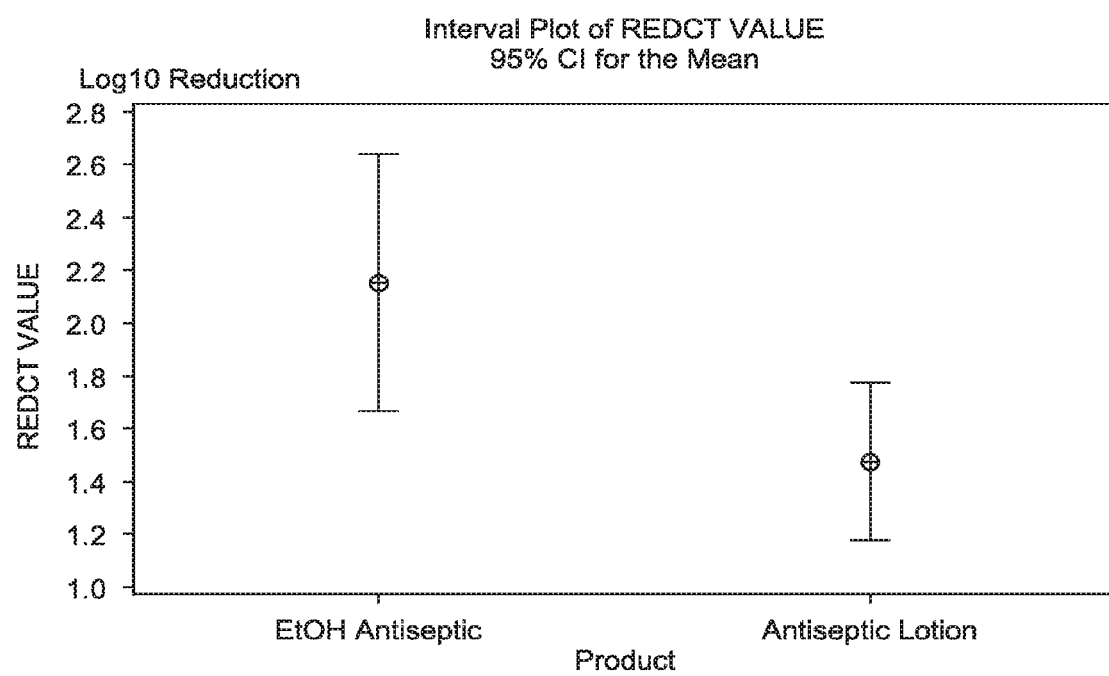
FIG. 4 depicts data comparing the antimicrobial effectiveness (against *S. marcescens*) of one embodiment of an alcohol-based sanitizing formulation disclosed herein as compared to one embodiment of an antiseptic lotion formulation disclosed herein.

A one-way ANOVA was performed to compare the efficacy of the EtOH Antiseptic and the Antiseptic Lotion. The results of the F-test (calculations not shown) indicated that the two antiseptics were statistically distinct (p value of 0.012, with p<0.05 being significant). With the sample size of 6, the 95% Confidence Intervals of the Standard Deviation were calculated (see Table 22) and are depicted graphically in FIG. 4. Based on the overlapping 95% confidence intervals, both products were the same in this evaluation, therefore post-hoc analysis (the Tukey Method) was applied. Based on the post-hoc analysis, the EtOH antiseptic was found to result in greater antimicrobial effects. However, depending on the microorganism tested, in several embodiments the two formulations may perform equivalently, and in still additional embodiments, the Antiseptic Lotion may outperform the EtOH Antiseptic. In summary, however, these data demonstrate that both the alcohol-based antiseptic and the water based antiseptic lotion, according to several formulations disclosed herein, result in substantial reductions in bacterial load with just a single application. These results indicate that, according to several embodiments, even a single application of can yield significant antimicrobial effects. This efficacy is particularly important in many environments in which, for example, repeated application is inefficient or impossible. In such cases, the efficacy of the disclosed formulations ensure a significant anti-microbial effect, even with a single application, which may be the difference between stoppage and transmission of microorganisms. Moreover, these results are particularly unexpected in view of the reduced volume (0.4 mL) of the formulations that were used. Thus, in several embodiments, the efficacy of the formulations disclosed herein is sufficient to allow smaller volumes of use. In several embodiments, this results in better user compliance. In several embodiments, this also reduces costs, without sacrificing efficacy.

Example 8—Extended Antimicrobial Efficacy of Sanitizing Formulations

As discussed above, several embodiments of the formulations disclosed herein result in rapid and broad-efficacy antimicrobial effects. However, many currently available and standard alcohol sanitizers and antibacterial soaps do not provide extended protection against microbes. For example, once the alcohol evaporates or the soap is rinsed off, hands can immediate become re-contaminated when they make contact with a contaminated surface. This presents a significant limitation to effective hand hygiene, as even in healthcare settings, highly trained workers only comply with hand hygiene protocol 40% of the time with alcohol sanitizers, and compliance with handwashing is even lower. Thus, several embodiments of the formulations disclosed herein are designed with persistence as well as efficacy in mind, in order to maximize the antimicrobial effect achieved when workers (or other types of users) utilize a sanitizing formulation, even if that use is less frequent than recommendations or in some embodiments, just a single application. The present example tested products for both immediate kill and continued protection of the hands against transient bacteria. The products tested were alcohol-based Antiseptic (comprising, according to one embodiment, 70% ethanol w/v, EtOH Antiseptic), an Antiseptic Lotion (comprising, according to one embodiment, 0.2% BZT; Antiseptic Lotion), and a Foaming Hand Soap (comprising, according to one embodiment, 0.2% BZT, Foaming Soap).

The testing utilized a modification of the ASTM1882 method, which employs a standard pigskin model as a substitute for human skin. The products were applied as they would be used, according to several embodiments, with the EtOH Antiseptic and Antiseptic Lotion tested as leave-on products and the Foaming Hand Soap lathered between two pigskin pieces and then rinsed clean. Testing was performed against *Staphylococcus aureus* and *Escherichia coli* to test against both a gram-positive and gram-negative bacteria, respectively.

The modified ASTM method 1882 was used, as detailed below. All control and test samples were performed in triplicate. Pigskin samples were cleaned with 70% ethanol and allowed to dry. A control was performed by rubbing a mild non-antibacterial soap (e.g., Ivory Soap) on a 4×4 cm² portion of pigskin for 20 seconds, then rinsing clean the pigskin and patting it dry. The EtOH Antiseptic and Antiseptic Lotion were rubbed on individual 4×4 cm² portions of pigskin for 20 seconds and allowed to dry on the pigskin. The Foaming Soap was applied, rubbed between two pigskin samples, and then rinsed completely off and patted dry. After being left undisturbed for a pre-determined sampling time (2 minutes, 1 hour, 4 hours, and 8 hours (8 hours not tested for Foaming Soap in this Example)), the treated pigskin was then pressed onto an inoculated plate containing either *S. aureus* or *E. coli* organisms for 5 seconds, then pressed onto a fresh, un-inoculated test plate for 5 seconds. All testing was performed in triplicate. The un-inoculated test plates were incubated overnight (e.g., about 10-20 hours) at about 37° C. and colonies were counted the following day.

Figure 5:
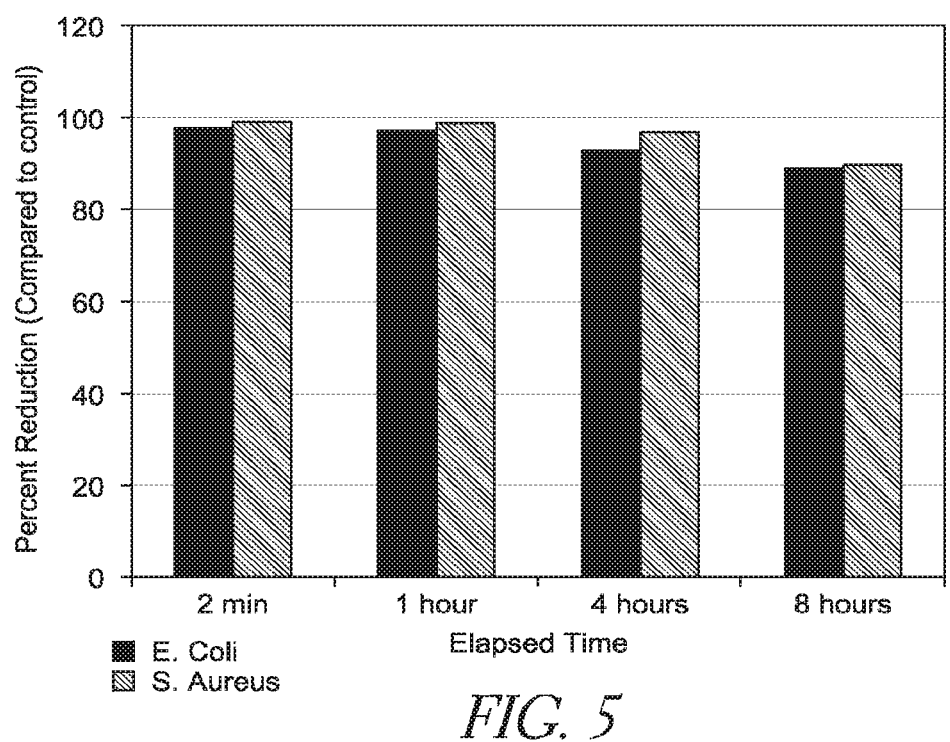
FIG. 5 depicts data related to the sustained antimicrobial effectiveness of one embodiment of an alcohol-based antiseptic against either *E. coli* or *S. aureus*.

The results for the antimicrobial effects of the EtOH Antiseptic against *S. aureus* or *E. coli* are shown in Table 23 and FIG. 5.

TABLE 23

Persistent Antimicrobial Efficacy of EtOH Antiseptic

| Time Point | S. Aureus Percent Reduction* | S. Aureus log Reduction | E. Coli Percent Reduction** | E. Coli log Reduction |
|---|---|---|---|---|
| 2 minutes | 99 | 1.87 | 98 | 1.65 |
| 1 hour | 99 | 2.14 | 97 | 1.34 |
| 4 hours | 97 | 1.62 | 93 | 1.15 |
| 8 hours | 90 | 0.99 | 89 | 0.95 |

Figure 6:
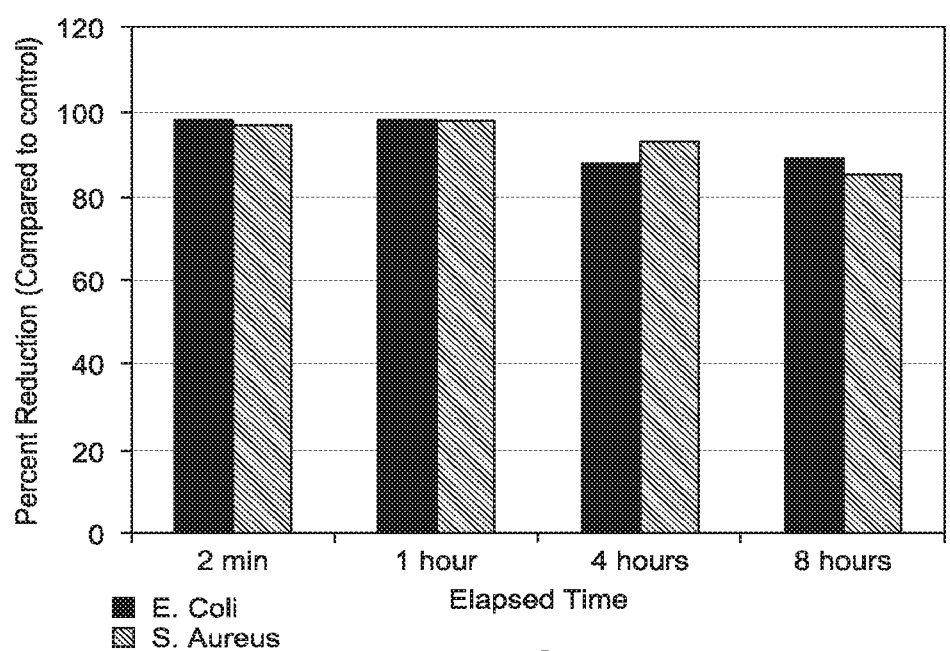
FIG. 6 depicts data related to the sustained antimicrobial effectiveness of one embodiment of an antiseptic lotion against either *E. coli* or *S. aureus*.

*Initial inoculum of *S. aureus* of $2 \times 10^3$
**Initial inoculum of *E. coli* of $5 \times 10^3$ The results for the antimicrobial effects of the Antiseptic Lotion against *S. aureus* or *E. coli* are shown in Table 24 and FIG. 6.

TABLE 24

Persistent Antimicrobial Efficacy of Antiseptic Lotion

| Time Point | S. Aureus Percent Reduction* | S. Aureus log Reduction | E. Coli Percent Reduction** | E. Coli log Reduction |
|---|---|---|---|---|
| 2 minutes | 97 | 1.6 | 98 | 1.80 |
| 1 hour | 98 | 1.85 | 98 | 1.71 |
| 4 hours | 93 | 1.16 | 88 | 0.92 |
| 8 hours | 85 | 0.84 | 89 | 0.98 |

*Initial inoculum of *S. aureus* of $2 \times 10^3$
**Initial inoculum of *E. coli* of $5 \times 10^3$ The results for the antimicrobial effects of the Foaming Soap against *S. aureus* are shown in Table 25.

TABLE 25

Persistent Antimicrobial Efficacy of Foaming Soap

| Time Point | S. Aureus Percent Reduction* | S. Aureus log Reduction |
|---|---|---|
| 2 minutes | 97.6 | 1.63 |
| 1 hour | 97.8 | 1.67 |
| 4 hours | 95.4 | 1.34 |

*Initial inoculum of *S. aureus* of $2 \times 10^3$

These data demonstrate that each of the formulations tested for persistence against *S. aureus* and/or *E. coli* exhibited substantial extended antimicrobial activity. Little loss of efficacy was detected in any of the products, even for up to eight hours after application, which likely extends well beyond the period in time in which a subject's hand or hands would go without some method of cleansing or disinfecting. There was no notable loss in efficacy between the rapid-kill time frames tested (see e.g., Example 5 above) and the 2 minute time point tested, and the reduction of *S. aureus* or *E. Coli* at 2 minutes was significant. Moreover, the EtOH Antiseptic and Antiseptic Lotion had only nominal reductions in efficacy after 1 hour, and only a 2-10% drop-off after 4 hours. The Foaming Hand Soap, even after it had been rinsed from the pigskin model, showed similar efficacy, with no drop in performance an hour after application, and only a 2% drop after four hours. Carried out to 8 hours, the EtOH Antiseptic and the Antiseptic Lotion showed a slightly reduced efficacy of 90% reduction and 85% reduction in *S. aureus* (respectively) and an 89% reduction in *E. coli*. The long term efficacy of each of these formulations (e.g., 4 hours and longer) is particularly unexpected given that the products are not directly contacted with the bacteria (at least in the same fashion as in the rapid-kill test), but rather the surface of the skin is "pre-treated". Thus, in several embodiments, the application of one or more of the formulations disclosed herein functions in a prophylactic fashion, not only killing microorganisms present on the surface (e.g., the hand) but also reducing the likelihood of microorganisms re-colonizing that surface. Such preventative effects aid in reducing transmission of microorganisms and thereby decrease the chance of spreading infection from person to person (either directly or via contact with another surface).

The present example used a standardized method, thereby allowing retrospective comparison with the persistence of several alternative commercial products. In 2006, a study demonstrated that (again with the same protocol) Avagard (3M), Prevacare (J&J) and Triseptin (Healthpoint) showed efficacy ranging from 17%-67% reductions in transient bacteria when tested at 20 or 35 minutes. Surprisingly, the formulations tested in the present example all demonstrate more than 97% reduction in microorganisms at 1 hour and 88% (or more) at 4 hours (Shintre et al., Int. J. of Hygiene and Environ. Health, 2006).

Thus, the formulations according to several embodiments herein exhibit significant antimicrobial properties against both gram-positive and gram-negative, transient bacteria at time points up to eight hours after initial application. This extended efficacy unexpected given that this is based on a single application (and in the case of the Foaming Soap, a single application followed by rinsing). This extended protection, in several embodiments, may be clinically significant, as circumstances may limit the adherence to hand hygiene protocols. However the formulations disclosed herein, based at least in part on their persistent effects, may significantly reduce the transmission of pathogens and illness, thereby lowering infection rates in, for example, schools, shopping areas or healthcare facilities, as well as in the general population and various other environments where microorganism colonization and/or transmission could occur.

Example 9—Comparison of Extended Antimicrobial Efficacy Foaming Soap Versus Standard Soaps Building on the data above related to the extended efficacy of several of the formulations disclosed herein, the present example was performed to compare the long-term antimicrobial activity of the Foaming Soap according to several embodiments disclosed herein against other common soaps on the market. The soaps tested were Foaming Soap as disclosed herein, comprising benzethonium Chloride, 0.2% BZT, Brand 2 antibacterial soap comprising 0.2% benzalkonium chloride, an antibacterial scrub comprising 0.4% chlorhexidine gluconate, and Lifebuoy, a soap comprising phenol as an antibacterial agent.

Testing was performed at 2 minutes, 1 hour, and 6 hours after application of the various soaps to determine how the persistent effect of the products changed with time. As discussed in Example 8 above, the testing utilized a modification of the ASTM 1882 method, using pigskin as a substitute for human skin. The products were applied as they would be used, with the soaps rinsed off after application. Testing was performed against *Escherichia coli*.

Pigskin samples were cleaned with 70% ethanol and allowed to dry. A control was performed by rubbing a mild non-antibacterial soap (e.g., Ivory Soap) on a 4×4 cm² portion of pigskin for 20 seconds, then rinsing clean the pigskin and patting it dry. The various soaps were applied to two pigskin samples, which were rubbed together for 20 seconds, and then rinsed completely off and patted dry. After being left undisturbed for a pre-determined sampling time (2 minutes, 1 hour, 6 hours), the treated pigskin was then pressed onto an inoculated plate containing *E. coli* organisms for 5 seconds, then pressed onto a fresh, un-inoculated test plate for 5 seconds. All testing was performed in triplicate. The un-inoculated test plates were incubated overnight (e.g., about 10-20 hours) at about 37° C. and colonies were counted the following day.

Figure 7:
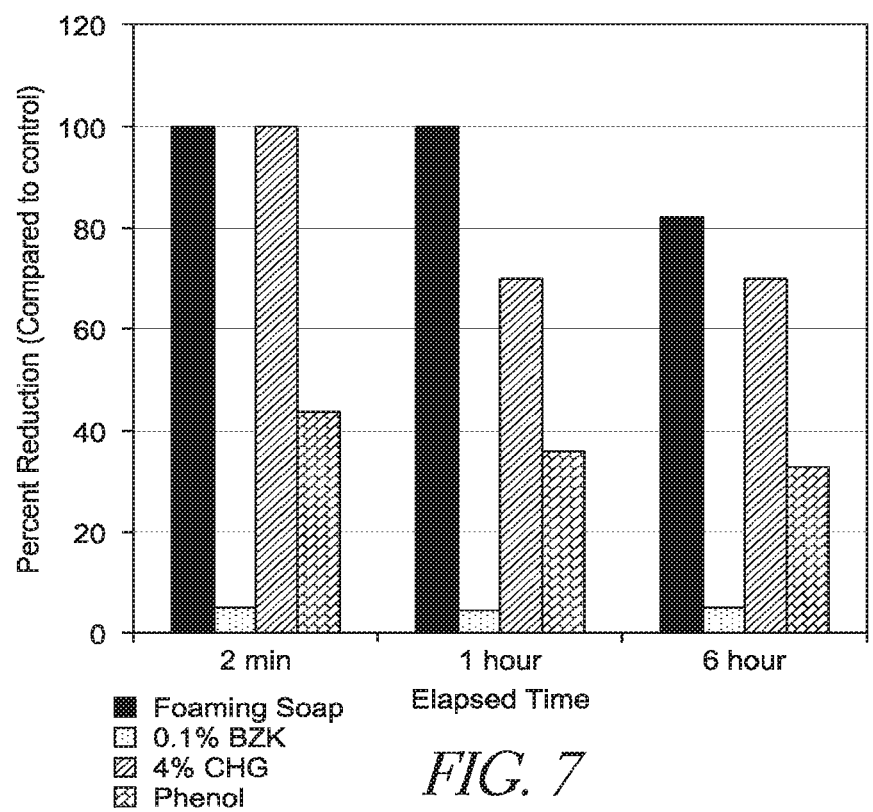
FIG. 7 depicts data related to the sustained antimicrobial effectiveness of various soaps, including one embodiment of a foaming soap disclosed herein, against *E. coli*.

The results for the comparison of persistent antimicrobial effects of the various soaps is shown in Table 26 and FIG. 7.

TABLE 26

Persistent Antimicrobial Efficacy of Soaps Against *E. Coli*.

| Time Point | Foaming Soap | | 0.1% BZK Soap | | 4% CHG Scrub | | Phenol | |
|---|---|---|---|---|---|---|---|---|
| | Percent Reduction | log Reduction | Percent Reduction | log Reduction | Percent Reduction | log Reduction | Percent Reduction | log Reduction |
| 2 minutes | 100 | 3.55 | 5.0 | 0.03 | 100 | 3.6 | 44 | 0.27 |
| 1 hour | 100 | 3.63 | 4.5 | 0.02 | 70 | 0.53 | 36 | 0.20 |
| 6 hours | 82 | 0.74 | 5.0 | 0.04 | 70 | 0.53 | 33 | 0.17 |

* Initial inoculum of *E. coli* of $5 \times 10^3$

These results demonstrate that, while several soaps offer modest to good antimicrobial efficacy in the short term, the Foaming Soap formulation, as disclosed herein, significantly outperforms the other soaps tested at both 1 hour and 6 hours post-application. Thus, as discussed above, the Foaming Soap not only offers the benefits of a short-term (e.g., rapid) antimicrobial effect, but also the longer term persistent effect, which (unexpectedly in view of the product being washed off) aids in preventing of re-growth of any remaining microorganisms as well as limiting the re-colonization of the surface with additional microorganisms.

Example 10—Comparison of Efficacy of Soap Formulations Against Drug-Resistant Bacteria Methicillin-resistant *Staphylococcus aureus* (MRSA) is responsible for several difficult-to-treat infections in humans. MRSA are strains of *S. aureus* that have developed, resistance to beta-lactam antibiotics, such as penicillins and cephalosporins. While the resistance itself does not equate with higher degree of virulence as compared to sensitive strains, the resistance does make MRSA infection more difficult to treat with standard types of antibiotic. MRSA infections are present particular issues in hospitals, nursing homes, and other similar environments where person to person contact is high and individuals may have one or more of open wounds, invasive devices, and/or weakened immune systems. In combination, these can present a population of individuals that are at greater risk of infection than the general public, and therefore proper hygiene to reduce and/or prevent infections, in particular MRSA infections, is of paramount importance.

The present study, therefore, was performed to assess the efficacy of certain sanitizing formulations as disclosed herein against MRSA. The protocol was as performed in Example 9 above, in brief, pigskin samples were cleaned with 70% ethanol and allowed to dry. A control was performed by rubbing a mild non-antibacterial soap (e.g., Ivory Soap) on a 4×4 cm² portion of pigskin for 20 seconds, then rinsing clean the pigskin and patting it dry. The various soaps were applied to two pigskin samples, which were rubbed together for 20 seconds, and then rinsed completely off and patted dry. After being left undisturbed for a pre-determined sampling time (2 minutes, 1 hour, and 6 hours), the treated pigskin was then pressed onto an inoculated plate containing MRSA for 5 seconds, then pressed onto a fresh, un-inoculated test plate for 5 seconds. All testing was performed in triplicate. The un-inoculated test plates were incubated overnight (e.g., about 10-20 hours) at about 37° C. and colonies were counted the following day.

Figure 8:
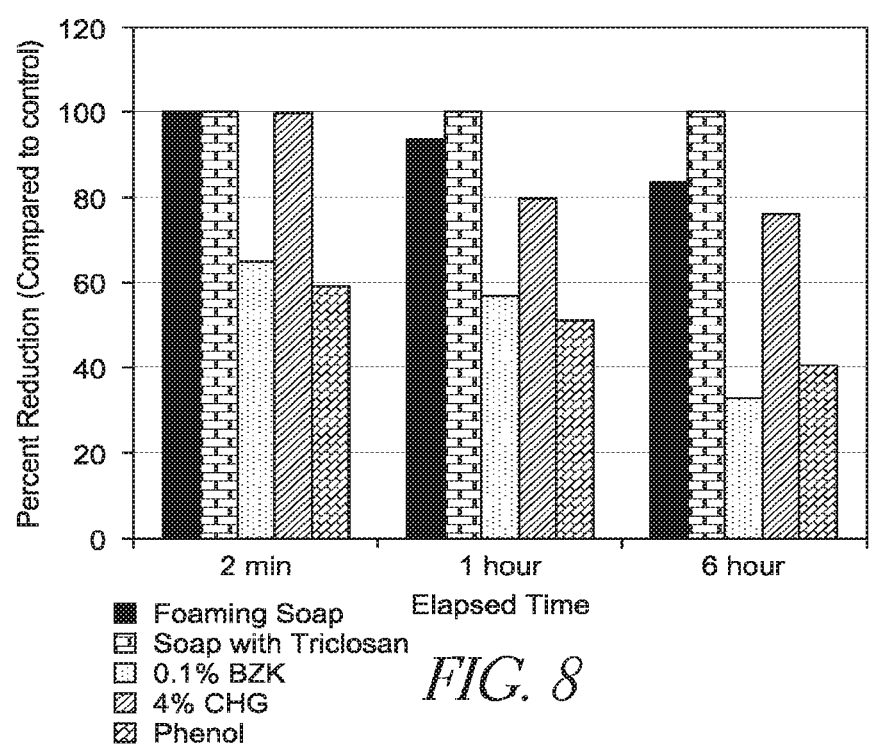
FIG. 8 depicts data related to the sustained antimicrobial effectiveness of various soaps, including one embodiment of a foaming soap disclosed herein, against MRSA.

The soaps tested were Foaming Soap as disclosed herein, comprising benzethonium Chloride, 0.2% BZT, Brand 1 antibacterial soap comprising triclosan; Brand 2 antibacterial soap comprising 0.2% benzalkonium chloride, an antibacterial scrub comprising 0.4% chlorhexidine gluconate, and Lifebuoy, a soap comprising phenol as an antibacterial agent. The results from these experiments are summarized in Table 27 and shown in FIG. 8.

TABLE 27

Antimicrobial Efficacy of Soaps Against MRSA

| Product | | 2 minutes | 1 hour | 6 hours |
|---|---|---|---|---|
| Foaming Soap | % Reduction | 99.8 | 93.4 | 83.5 |
| | Log Reduction | 2.68 | 1.26 | 0.78 |
| Brand 1 Soap with Triclosan | % Reduction | 100 | 100 | 100 |
| | Log Reduction | 3.70 | 3.76 | 3.78 |
| 0.1% BZK Soap | % Reduction | 64.7 | 56.7 | 32.9 |
| | Log Reduction | 0.5 | 0.46 | 0.18 |
| 4% CHG Scrub | % Reduction | 99.7 | 79.7 | 76.1 |
| | Log Reduction | 2.54 | 0.69 | 0.62 |
| Phenol Soap | % Reduction | 58.8 | 50.9 | 40.6 |
| | Log Reduction | 0.4 | 0.31 | 0.23 |

These data demonstrate that the Foaming Soap, according to several embodiments disclosed herein, significantly outperforms several antibacterial products presently available, in particular when considering the duration of antimicrobial effects. For example, the Foaming Soap killed nearly 100% of the MRSA at 2 minutes, with the efficacy only slightly diminishing at 1 hour. At 6 hours, the Foaming Soap still was able to reduce the MRSA by over 80%. In contrast, soap with 0.1% BZK and phenol-containing soap achieved only 64.7% and 58.8% reduction in MRSA at 2 minutes. This efficacy is not only substantially less than the Foaming Soap, but it also is reduced over time, with the 0.1% BZK formulation achieving only a 32.9% reduction at 6 hours, and the phenol-containing soap achieving only 40.6 reduction in MRSA at 6 hrs. The scrub containing 4% chlorhexidine gluconate results in substantially similar antimicrobial effects at 2 minutes (99.7 versus 99.8 for the Foaming Soap), however, like the above-mentioned products, the efficacy of the 4% CHG scrub drops off significantly by 1 hour (to 79.7% reduction). At six hours post-application, the 4% CHG scrub achieved a 76.1% reduction, which is improved as compared to the above-mentioned products, but is still less than the reduction achieved by the Foaming Soap. The Foaming Soap was not as effective as the Brand 1 soap containing triclosan, which had 100% reduction at all times tested. However, as discussed above, the foaming soap formulations are, in several embodiments, triclosan-free, which, based on the data above, advantageously allows efficacious antimicrobial effects without the adverse effects associated with triclosan. Moreover, the Foaming Soap provides an unexpectedly robust effect against MRSA, particularly for an extended duration, and with a reduced, and in several embodiments, nonexistent, risk of the development of microbial resistance to the efficacy of the formulation.

Example 11—Comparison of Efficacy of Leave-On Antiseptic Formulations Against Drug-Resistant Bacteria As discussed above, MRSA infections present a particular problem in certain environments, such as hospitals, nursing homes, etc., because of the more difficult regime needed to combat the infections. Preventing the development and/or spread of infections would reduce the associated morbidity and mortality related to MRSA infections.

Figure 9:
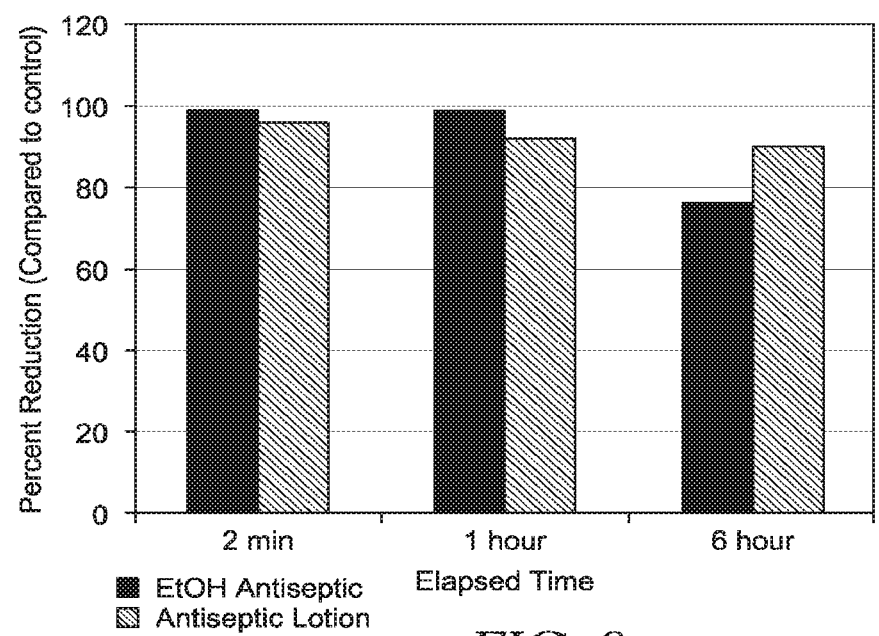
FIG. 9 depicts data related to the sustained antimicrobial effectiveness of one embodiment of an alcohol-based sanitizing formulation disclosed herein as compared to one embodiment of an antiseptic lotion formulation disclosed herein, against MRSA.

The present study, therefore, was performed to assess the efficacy of certain leave on sanitizing formulations as disclosed herein against MRSA (as opposed to the soaps tested in Example 10, which are used and then removed by rinsing). The protocol was as performed in Example 9 above. The EtOH Antiseptic and Antiseptic Lotion were rubbed on individual 4×4 $cm^2$ portions of pigskin for 20 seconds and allowed to dry on the pigskin. After being left undisturbed for a pre-determined sampling time (2 minutes, 1 hour, or 6 hours the treated pigskin was then pressed onto an inoculated plate containing MRSA for 5 seconds, then pressed onto a fresh, un-inoculated test plate for 5 seconds. All testing was performed in triplicate. The un-inoculated test plates were incubated overnight (e.g., about 10-20 hours) at about 37° C. and colonies were counted the following day. The results from these experiments are summarized in Table 28 and depicted in FIG. 9.

TABLE 28

Antimicrobial Efficacy of Leave-on Sanitizing Formulations Against MRSA

| Product | | 2 minutes | 1 hour | 6 hours |
|---|---|---|---|---|
| EtOH Antiseptic | % Reduction | 99.4 | 94.4 | 76.3 |
| | Log Reduction | 1.85 | 1.26 | 0.63 |
| Antiseptic Lotion | % Reduction | 96.4 | 92.0 | 90 |
| | Log Reduction | 1.45 | 1.08 | 1.02 |

These data demonstrate that the alcohol-based antiseptic and the antiseptic lotion, according to several embodiments disclosed herein, achieve considerable antimicrobial effects against MRSA, even at extended elapsed times after application. Both formulations were nearly 100% effective at reducing MRSA at 2 minutes, with the efficacy only slightly diminishing at 1 hour. At 6 hours, the alcohol-based antiseptic still achieves a 76.3 percent reduction in MRSA. This may be a result of the evaporation of the alcohol during the elapsed 6 hours between application of the formulation and contact with the MRSA. However, given the significant morbidity and mortality related to MRSA infection and transmission, this reduction at 6 hours may still have clinical relevance. The Antiseptic Lotion was still able to reduce MRSA by 90% at 6 hours, which, in several embodiments, advantageously allows the Antiseptic Lotion to reduce risk of MRSA infection/transmission over an extended period of time. This persistence (of both formulations) may help compensate for situations in which there is a risk of MRSA exposure, but recommended hygiene practices are not followed. Also, in several embodiments, these formulations achieve these effects with limited risk of development of resistance by the MRSA.

Example 12—Comparison of Efficacy of Antiseptic Formulations Against Norovirus

As discussed above, various bacterial or viral outbreaks in certain environments can cause widespread illness. For example, human norovirus is one of the most common causes of acute viral gastroenteritis, causing about 6 million clinical cases worldwide, including nearly 200,000 deaths annually. Cruise ships, schools, health care settings, and other settings in which individuals are in close and or repeated contact with one another present environments where transmission and spread of infection can occur rapidly.

The study described below will evaluate the virucidal efficacy of several of the sanitizing formulations disclosed herein as compared to a control when the formulations are challenged with a human Norovirus surrogate. One such surrogate is *Feline Calicivirus* strain F9 (FCV; ATCC #VR-782). Human subjects are to be used in this study. The methodology for this is to be based on the Standard Test Method for Determining the Virus-Eliminating Effectiveness of Hygienic Handwash and Handrub Agents Using the Fingerpads of Adults, ASTM E 1838-10.

Feline kidney cells, such as for example ATCC #CCL-94 (or other suitable host cells) are to be maintained as mono layers. Cells will be grown to approximately 90% confluency and are to be less than 48 hours old before being inoculation with virus. On the day of use, aliquots of the stock FCV virus are to be prepared with 5% Fetal Bovine Serum (FBS) as an Organic Soil Load. Hard water (to be prepared according to accepted Standard Operating Procedures) is to be used as a control. Control evaluations of virus susceptibility (test sensitivity of cells to virus) will be performed. Control evaluations of the test/product neutralizer (e.g., neutralizer effect on cell susceptibility to virus) will be performed.

Each subject will be in testing for 3 to 4 hours on a single day. Subjects will clip their fingernails to a free edge of approximately 1 mm and all jewelry is to be removed from the hands and arms prior to washing. Subjects will use protective garments and a face shield. Each subject will perform a 30-second handwash using a nonmedicated soap to remove dirt and oil from the hands, which will be followed by a 30-second rinse. During this handwash, the subjects will not be allowed to touch any part of the sink. The subjects will then dry their hands using a clean paper towel and will receive into their cupped hands 5 milliliters of 70% ethanol. The subjects will distribute the over the surfaces of both of their hands by rubbing them together until dry.

Input Control

The thumbpads of each subject are to be demarcated, by, for example, pressing them to the open ends of screw-cap vials. This procedure will leave circular imprints on the thumbpads outlining the target areas for exposure. Each thumbpad will be contaminated with virus suspension (e.g., ~10 μL) and will be eluted immediately using a neutralizer/elution solution. Maintenance Medium with 0.1% Tween 80 will be used as the neutralizer/elution solution. The screw-cap vials containing 1.0 mL of the neutralizer/elution solution will be inverted over the contaminated thumbpads and will be held for approximately 5 seconds. The screw-cap vials will then be repeatedly inverted and held for 5 seconds 20 times in succession. The mouths of the screw-cap vials will be removed from the thumbpads, scraping the inside lips of the vials against the skin in an upward motion to recover as much fluid as possible. The thumbpads will then be decontaminated by pressing them for 3 minutes into a paper towel saturated with 5 mL of 70% ethanol, followed by an air-dry.

Baseline Control

Two randomly selected fingerpads (one from each hand) will be demarcated as above. Each fingerpad will be contaminated with 10 μL of virus suspension and allowed to air-dry under ambient conditions. Each fingerpad will then be placed over the mouth of a screw-cap vial containing 1.0 mL of the neutralizer/elution solution and sampled using the procedure described above (multiple, repeated inversions).

Test Material Efficacy

Two randomly selected fingerpads (one from each hand) will be demarcated as above. Each designated fingerpad will be contaminated with 10 μL of virus suspension and allowed to air dry under ambient conditions. Each virus-contaminated fingerpad will be placed over the mouth of a vial containing test product and inverted. The test product will remain in contact with the contaminated area for approximately 10 seconds, and the vials will then be inverted 10 times in quick succession. Upon the completion of exposure, the mouths of the screw-cap vials will be removed from the fingerpads. Each fingerpad will then be placed over the mouth of a screw-cap vial containing 1.0 mL of the neutralizer/elution solution and will be sampled using the procedure described above. Controls (e.g., hard water) will be performed in the same fashion.

Results

In several embodiments, the antiseptic formulations tested will result in substantial reduction in viral infectivity. In several embodiments, the reductions will be statistically greater than that achieved by the control. In several embodiments, the reductions based on the application of the antiseptic formulations disclosed herein will be at least 2, will be at least 3, will be at least 3.5, will be at least 4 (or greater) $\log_{10}$ reductions in viral infectivity.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. For all of the embodiments described herein the steps of the methods need not be performed sequentially. Thus, it is intended that the scope of the inventions herein disclosed should not be limited by the particular disclosed embodiments described above.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 micrograms" includes "10 micrograms.

What is claimed is:

1. A foaming soap comprising, by weight:
   about 50.0% to about 65.0% water;
   about 5.0% to about 20.0% ethyl alcohol;
   about 0.005% to about 0.1% polyquaternium-10;
   about 0.1% to about 2.0% citric acid;
   about 0.1% to about 2.0% zinc gluconate;
   about 0.05% to about 2.0% benzethonium chloride; and
   about 0.1% to about 1.0% farnesol.

2. The foaming soap of claim 1, which comprises, by weight, about 10.0% ethyl alcohol.

3. The foaming soap of claim 1, which comprises, by weight, about 0.01% polyquaternium-10.

4. The foaming soap of claim 1, which comprises, by weight, about 0.2% benzethonium chloride.

5. The foaming soap of claim 1, which comprises, by weight, about 0.5% farnesol.

6. The foaming soap of claim 1, which comprises, by weight, about 0.7% citric acid.

7. The foaming soap of claim 1, which comprises, by weight, about 0.3% zinc gluconate.

8. The foaming soap of claim 1, which comprises, by weight:
   about 50.0% to about 65.0% water;
   about 10.0% ethyl alcohol;
   about 0.01% polyquaternium-10;
   about 0.7% citric acid;
   about 0.3% zinc gluconate;
   about 0.2% benzethonium chloride; and
   about 0.5% farnesol.

9. The foaming soap of claim 1, further comprising butylene glycol, lauramine oxide (LO), cocamiopropyl betaine, sodium chloride), cetrimonium chloride, PPG-2 hydroxyethyl cocamide, methylchloroisothiazolinone, glycerin, water aloe barbadensis leaf extract, a fragrance, and polyaminopropyl biguanide.

10. The foaming soap of claim 9, which comprises, by weight, about 0.5% to about 2.0% butylene glycol.

11. The foaming soap of claim 9, which comprises, by weight, about 5.0% to about 10.0% mackamine LO which comprises water and lauramine oxide.

12. The foaming soap of claim 9, which comprises, by weight, about 5.0% to about 10.0% caltaine C-35 which comprises water, cocamiopropyl betaine, and sodium chloride.

13. The foaming soap of claim 9, which comprises, by weight, about 3.0% to about 10.0% carsoquat CT-429 which comprises water and cetrimonium chloride.

14. The foaming soap of claim 9, which comprises, by weight, about 1.0% to about 5.0% PPG-2 hydroxyethyl cocamide.

15. The foaming soap of claim 9, which comprises, by weight, about 0.01% to about 1.0% methylchloroisothiazolinone.

16. The foaming soap of claim 9, which comprises, by weight, about 0.05% to about 1.0% actiphyte of aloe vera which comprises glycerin and water aloe barbadensis leaf extract.

17. The foaming soap of claim 9, which comprises, by weight, about 0.01% to about 0.5% cosmocil CQ which comprises water and polyaminopropyl biguanide.

18. The foaming soap of claim 1, which comprises, by weight:
- about 50.0% to about 65.0% water;
- about 5.0% to about 20.0% ethyl alcohol;
- about 0.05% to about 2.0% benzethonium chloride;
- about 0.1% to about 1.0% farnesol;
- about 0.005% to about 0.1% polyquaternium-10;
- about 0.1% to about 2.0% citric acid;
- about 0.5% to about 2.0% butylene glycol;
- about 0.1% to about 2.0% zinc gluconate;
- about 0.05% to about 2.0% benzethonium chloride;
- about 5.0% to about 10.0% mackamine LO;
- about 5.0% to about 10.0% caltaine C-35;
- about 3.0% to about 10.0% carsoquat CT-429;
- about 1.0% to about 5.0% PPG-2 hydroxyethyl cocamide;
- about 0.01% to about 1.0% methylchloroisothiazolinone;
- about 0.05% to about 1.0% actiphyte of aloe vera;
- about 0.01 to about 0.10% of the fragrance; and
- about 0.01% to about 0.5% cosmocil CQ.

* * * * *